US010342617B2

(12) United States Patent
Weckwerth et al.

(10) Patent No.: US 10,342,617 B2
(45) Date of Patent: *Jul. 9, 2019

(54) PHOTOTHERAPY DEVICE THERMAL CONTROL APPARATUS AND METHOD

(71) Applicant: Channel Investments, LLC, Tampa, FL (US)

(72) Inventors: Mark V. Weckwerth, Pleasonton, CA (US); Tobin C. Island, Oakland, CA (US); Robert E. Grove, Pleasanton, CA (US)

(73) Assignee: CHANNEL INVESTMENTS, LLC, Tampa, FL (US)

( * ) Notice: Subject to any disclaimer, the term of this patent is extended or adjusted under 35 U.S.C. 154(b) by 760 days.

This patent is subject to a terminal disclaimer.

(21) Appl. No.: 14/047,998

(22) Filed: Oct. 7, 2013

(65) Prior Publication Data

US 2014/0171929 A1    Jun. 19, 2014

Related U.S. Application Data

(63) Continuation of application No. 11/545,963, filed on Oct. 10, 2006, now Pat. No. 8,511,104, which is a (Continued)

(51) Int. Cl.
*A61B 18/20* (2006.01)
*A61B 17/00* (2006.01)
(Continued)

(52) U.S. Cl.
CPC .. *A61B 18/203* (2013.01); *A61B 2017/00057* (2013.01); *A61B 2017/00061* (2013.01);
(Continued)

(58) Field of Classification Search
CPC .............. A61B 18/20; A61B 2018/203; A61B 2018/00452; A61B 2018/00476
(Continued)

(56) References Cited

U.S. PATENT DOCUMENTS 3,307,533 A    3/1967    Meredith et al. ............. 601/150
3,538,919 A    11/1970   Meyer ............................ 606/36
(Continued)

FOREIGN PATENT DOCUMENTS

CN    2442726 Y    8/2001    ............. A63H 33/00
DE    19629978 A1  1/1998    ............. F41A 33/02
(Continued)

OTHER PUBLICATIONS

European Office Action, Application No. 13159309.7, 4 pages, dated May 8, 2014.
(Continued)

*Primary Examiner* — Ahmed M Farah
(74) *Attorney, Agent, or Firm* — Slayden Grubert Beard PLLC

(57) ABSTRACT

A cordless, hand-held dermatologic hair-regrowth-inhibiting apparatus may include: a self-contained housing configured for gripping by a person's hand for cordless manipulation in a hair-regrowth-inhibiting procedure; a light source comprising one or more diode laser bars within the housing; a direct drive electrical circuit within the housing comprising one or more batteries for energizing the light source to produce output light pulses, wherein the electrical circuit does not include any storage capacitors that energize the light source by capacitor discharge; and a light path within the housing including an aperture through which the output light pulses are propagated out of the housing having properties sufficient for at least temporary hair-regrowth inhibition.

4 Claims, 12 Drawing Sheets

Related U.S. Application Data continuation of application No. 10/783,607, filed on Feb. 19, 2004, now Pat. No. 7,118,563.

(60) Provisional application No. 60/450,243, filed on Feb. 25, 2003, provisional application No. 60/450,598, filed on Feb. 26, 2003, provisional application No. 60/451,091, filed on Feb. 28, 2003, provisional application No. 60/452,304, filed on Mar. 4, 2003, provisional application No. 60/451,981, filed on Mar. 4, 2003, provisional application No. 60/452,591, filed on Mar. 6, 2003, provisional application No. 60/456,586, filed on Mar. 21, 2003, provisional application No. 60/458,861, filed on Mar. 27, 2003, provisional application No. 60/472,056, filed on May 20, 2003, provisional application No. 60/456,379, filed on Mar. 20, 2003.

(51) Int. Cl.
   *A61B 18/00* (2006.01)
   *A61B 18/22* (2006.01)
   *A61B 90/00* (2016.01)

(52) U.S. Cl.
   CPC ........... *A61B 2017/00066* (2013.01); *A61B 2017/00172* (2013.01); *A61B 2017/00734* (2013.01); *A61B 2018/00005* (2013.01); *A61B 2018/00452* (2013.01); *A61B 2018/00476* (2013.01); *A61B 2018/2261* (2013.01); *A61B 2090/065* (2016.02)

(58) Field of Classification Search
   USPC ............ 606/3, 9, 10; 607/88–91; 362/157, 362/183–185, 194; 438/142; 257/565, 257/629
   See application file for complete search history.

(56) References Cited

U.S. PATENT DOCUMENTS

| | | | |
|---|---|---|---|
| 3,622,743 A | 11/1971 | Muncheryan | 219/121.63 |
| 3,693,623 A | 9/1972 | Harte et al. | 606/9 |
| 3,821,510 A | 6/1974 | Muncheryan | 219/121.79 |
| 3,834,391 A | 9/1974 | Block | 128/303.1 |
| 4,140,130 A | 2/1979 | Storm, III | 607/154 |
| 4,232,678 A | 11/1980 | Skovajsa | 607/89 |
| 4,240,738 A | 12/1980 | Praamsma et al. | 355/1 |
| 4,354,092 A | 10/1982 | Manabe et al. | 219/225 |
| 4,388,924 A | 6/1983 | Weissman et al. | 606/9 |
| 4,423,736 A | 1/1984 | Dewitt et al. | 600/306 |
| 4,449,528 A | 5/1984 | Auth et al. | 606/31 |
| 4,551,628 A | 11/1985 | Grossman | 250/503.1 |
| 4,573,466 A | 3/1986 | Simada et al. | 606/11 |
| 4,592,353 A | 6/1986 | Daikuzono | 606/16 |
| 4,608,978 A | 9/1986 | Rohr | 606/9 |
| 4,617,926 A | 10/1986 | Sutton | 606/9 |
| 4,690,141 A | 9/1987 | Castel et al. | 607/90 |
| 4,733,660 A | 3/1988 | Itzkan | 606/9 |
| 4,829,262 A | 5/1989 | Furumoto | 359/346 |
| 4,846,184 A | 7/1989 | Comment et al. | 600/306 |
| 4,849,211 A | 7/1989 | Schrauzer | 424/45 |
| 4,860,744 A | 8/1989 | Johnson et al. | 606/31 |
| 4,905,690 A | 3/1990 | Ohshiro et al. | 607/89 |
| 4,930,504 A | 6/1990 | Diamantopoulos et al. | 607/88 |
| 5,057,104 A | 10/1991 | Chess | 606/9 |
| 5,059,013 A | 10/1991 | Jain | 359/503 |
| 5,059,192 A | 10/1991 | Zaias | 606/9 |
| 5,071,417 A | 12/1991 | Sinofsky | 606/8 |
| 5,075,971 A | 12/1991 | Mccambridge | 30/133 |
| 5,092,865 A * | 3/1992 | Rink | A61B 18/20 606/10 |
| 5,107,832 A | 4/1992 | Guibert et al. | 607/96 |
| 5,109,465 A | 4/1992 | Klopotek | 385/133 |
| 5,226,907 A | 7/1993 | Tankovich | 606/133 |
| 5,233,337 A | 8/1993 | Takahashi | 345/82 |
| 5,259,380 A | 11/1993 | Mendes et al. | 607/115 |
| 5,282,797 A | 2/1994 | Chess | 606/9 |
| 5,295,052 A | 3/1994 | Chin et al. | 362/580 |
| 5,344,418 A | 9/1994 | Ghaffari | 606/9 |
| 5,360,426 A | 11/1994 | Muller et al. | 606/13 |
| 5,401,270 A | 3/1995 | Muller et al. | 606/13 |
| 5,405,368 A | 4/1995 | Eckhouse | 607/88 |
| 5,425,728 A | 6/1995 | Tankovich | 606/9 |
| 5,431,647 A | 7/1995 | Purcell, Jr. et al. | 606/16 |
| 5,464,434 A | 11/1995 | Alt | 607/6 |
| 5,464,436 A | 11/1995 | Smith | 607/89 |
| 5,473,408 A | 12/1995 | Hoffman et al. | 355/53 |
| 5,481,385 A | 1/1996 | Zimmerman et al. | 349/62 |
| 5,486,172 A | 1/1996 | Chess | 606/20 |
| 5,519,534 A | 5/1996 | Smith et al. | 359/599 |
| 5,549,660 A | 8/1996 | Mendes et al. | 607/88 |
| 5,556,612 A | 9/1996 | Anderson et al. | 424/59 |
| 5,578,022 A | 11/1996 | Scherson et al. | 604/304 |
| 5,595,568 A | 1/1997 | Anderson et al. | 606/9 |
| 5,606,798 A | 3/1997 | Kelman | 30/41.5 |
| 5,611,798 A | 3/1997 | Eggers et al. | 606/31 |
| 5,624,435 A | 4/1997 | Furumoto et al. | 606/10 |
| 5,628,744 A | 5/1997 | Coleman et al. | 606/12 |
| 5,630,811 A | 5/1997 | Miller | 606/9 |
| 5,632,741 A | 5/1997 | Zavislan et al. | 606/9 |
| 5,643,252 A | 7/1997 | Waner et al. | 606/9 |
| 5,647,866 A | 7/1997 | Zaias et al. | 606/9 |
| 5,658,323 A | 8/1997 | Miller | 607/89 |
| 5,662,643 A | 9/1997 | Kung, V et al. | 606/3 |
| 5,669,916 A | 9/1997 | Anderson | 606/133 |
| 5,683,380 A | 11/1997 | Eckhouse et al. | 606/9 |
| 5,700,240 A | 12/1997 | Barwick, Jr. et al. | 604/22 |
| 5,707,403 A | 1/1998 | Grove et al. | 607/89 |
| 5,728,090 A | 3/1998 | Martin et al. | 606/3 |
| 5,735,844 A | 4/1998 | Anderson et al. | 606/9 |
| 5,743,901 A | 4/1998 | Grove et al. | 606/9 |
| 5,752,948 A | 5/1998 | Tankovich et al. | 606/9 |
| 5,752,949 A | 5/1998 | Tankovich et al. | 606/9 |
| 5,766,214 A | 6/1998 | Mehl, Sr. et al. | 606/9 |
| 5,769,844 A | 6/1998 | Ghaffari | 606/16 |
| 5,792,137 A | 8/1998 | Carr et al. | 606/29 |
| 5,814,040 A | 9/1998 | Nelson et al. | 606/9 |
| 5,817,089 A | 10/1998 | Tankovich et al. | 606/9 |
| 5,820,625 A | 10/1998 | Izawa et al. | 606/9 |
| 5,824,023 A | 10/1998 | Anderson | 607/88 |
| 5,830,208 A | 11/1998 | Muller | 606/9 |
| 5,843,072 A | 12/1998 | Furumoto et al. | 606/9 |
| 5,846,252 A | 12/1998 | Mehl, Sr. | 606/133 |
| 5,849,029 A | 12/1998 | Eckhouse et al. | 607/104 |
| 5,853,407 A | 12/1998 | Miller | 606/9 |
| 5,868,732 A | 2/1999 | Waldman et al. | 606/9 |
| 5,871,479 A | 2/1999 | Furumoto et al. | 606/9 |
| 5,871,480 A | 2/1999 | Tankovich | 606/9 |
| 5,871,521 A | 2/1999 | Kaneda et al. | 607/89 |
| 5,879,346 A | 3/1999 | Waldman et al. | 606/9 |
| 5,885,273 A | 3/1999 | Eckhouse et al. | 606/9 |
| 5,944,748 A | 8/1999 | Mager et al. | 607/88 |
| 5,966,210 A | 10/1999 | Rosow et al. | 356/213 |
| 5,968,034 A | 10/1999 | Fullmer et al. | 606/9 |
| 5,989,267 A | 11/1999 | Anderson | 606/133 |
| 6,015,404 A | 1/2000 | Altshuler et al. | 606/9 |
| RE36,634 E | 3/2000 | Ghaffari | 606/9 |
| 6,059,765 A | 5/2000 | Cole et al. | 604/500 |
| 6,072,551 A | 6/2000 | Jannson et al. | 349/64 |
| 6,080,146 A | 6/2000 | Altshuler et al. | 606/9 |
| 6,096,029 A | 8/2000 | O'donnell, Jr. | 606/9 |
| 6,104,959 A | 8/2000 | Spertell | 607/101 |
| 6,106,514 A | 8/2000 | O'donnell, Jr. | 606/9 |
| 6,114,862 A | 9/2000 | Tartagni et al. | 324/662 |
| 6,134,475 A | 10/2000 | Will | 607/98 |
| 6,138,041 A | 10/2000 | Yahia | 455/569.2 |
| 6,144,536 A | 11/2000 | Zimmerman et al. | 361/31 |
| 6,160,831 A | 12/2000 | Kleinschmidt et al. | 372/57 |
| 6,168,831 B1 | 1/2001 | Khan et al. | 427/240 |
| 6,171,301 B1 | 1/2001 | Nelson et al. | 606/9 |
| 6,183,500 B1 | 2/2001 | Kohler | 607/88 |

(56) References Cited

U.S. PATENT DOCUMENTS

| | | | |
|---|---|---|---|
| 6,183,773 B1 | 2/2001 | Anderson | 424/450 |
| 6,188,495 B1 | 2/2001 | Inoue et al. | 398/139 |
| 6,197,020 B1 | 3/2001 | O'donnell, Jr. | 606/9 |
| 6,208,749 B1 | 3/2001 | Gutkowicz-krusin et al. | 382/128 |
| 6,214,034 B1 | 4/2001 | Azar | 607/89 |
| 6,228,074 B1 | 5/2001 | Almeida | 606/9 |
| 6,251,127 B1 | 6/2001 | Biel | 607/88 |
| 6,264,649 B1 | 7/2001 | Whitcroft et al. | 606/22 |
| 6,269,818 B1 | 8/2001 | Lui et al. | 128/898 |
| 6,273,884 B1 | 8/2001 | Altshuler et al. | 606/9 |
| 6,273,885 B1 | 8/2001 | Koop et al. | 606/9 |
| 6,277,111 B1 | 8/2001 | Clement et al. | 606/9 |
| 6,280,438 B1 | 8/2001 | Eckhouse et al. | 606/9 |
| 6,290,713 B1 | 9/2001 | Russell | 607/88 |
| 6,306,130 B1 | 10/2001 | Anderson et al. | 606/27 |
| 6,322,584 B2 | 11/2001 | Ingle et al. | 607/96 |
| 6,379,376 B1 | 4/2002 | Lubart | 607/88 |
| 6,408,212 B1 | 6/2002 | Neev | 607/100 |
| 6,413,255 B1 | 7/2002 | Stern | 606/41 |
| 6,413,268 B1 | 7/2002 | Hartman | 607/94 |
| 6,428,198 B1 | 8/2002 | Saccomanno et al. | 385/147 |
| 6,436,127 B1 | 8/2002 | Anderson et al. | 607/89 |
| 6,440,122 B1 | 8/2002 | Shimoji | 606/2 |
| 6,441,943 B1 | 8/2002 | Roberts et al. | 359/267 |
| 6,451,007 B1 | 9/2002 | Koop et al. | 606/9 |
| 6,485,484 B1 | 11/2002 | Connors et al. | 606/9 |
| 6,494,900 B1 | 12/2002 | Salansky et al. | 607/89 |
| 6,508,813 B1 | 1/2003 | Alshuler | 606/9 |
| 6,511,475 B1 | 1/2003 | Altshuler et al. | 606/9 |
| 6,514,242 B1 | 2/2003 | Vasily et al. | 606/9 |
| 6,516,013 B1 | 2/2003 | Patzel et al. | 372/29.02 |
| 6,517,532 B1 | 2/2003 | Altshuler et al. | 606/9 |
| 6,533,775 B1 | 3/2003 | Rizoiu | 606/9 |
| 6,536,914 B2 | 3/2003 | Hoelen et al. | 362/231 |
| 6,548,781 B1 | 4/2003 | Brunwinkel | 219/121.73 |
| 6,563,853 B2 | 5/2003 | Heist et al. | 372/57 |
| 6,567,696 B2 | 5/2003 | Voznesensky et al. | 607/3 |
| 6,572,637 B1 | 6/2003 | Yamazaki et al. | 607/89 |
| 6,600,951 B1 | 7/2003 | Anderson | 604/20 |
| 6,605,080 B1 | 8/2003 | Altshuler et al. | 606/3 |
| 6,610,052 B2 | 8/2003 | Furumoto | 606/9 |
| 6,621,702 B2 | 9/2003 | Elias et al. | 361/700 |
| 6,637,924 B2 | 10/2003 | Pelka et al. | 362/555 |
| 6,641,044 B2 | 11/2003 | Plesko | 235/462.49 |
| 6,648,904 B2 | 11/2003 | Altshuler et al. | 607/96 |
| 6,653,618 B2 | 11/2003 | Zenzie | 250/221 |
| 6,659,999 B1 | 12/2003 | Anderson et al. | 606/9 |
| 6,660,000 B2 | 12/2003 | Neuberger et al. | 606/9 |
| 6,663,620 B2 | 12/2003 | Altshuler et al. | 606/9 |
| 6,663,659 B2 | 12/2003 | Mcdaniel | 607/88 |
| 6,666,856 B2 | 12/2003 | Connors et al. | 606/9 |
| 6,723,090 B2 | 4/2004 | Altshuler et al. | 606/9 |
| 6,733,493 B2 | 5/2004 | Gruzdev et al. | 606/9 |
| 6,749,624 B2 | 6/2004 | Knowlton | 607/104 |
| 6,758,845 B1 | 7/2004 | Weckwerth et al. | 606/9 |
| 6,790,205 B1 | 9/2004 | Yamazaki et al. | 606/9 |
| 6,808,287 B2 | 10/2004 | Lebens et al. | 362/184 |
| 6,817,997 B2 | 11/2004 | Furuno et al. | 606/9 |
| 6,872,221 B2 | 3/2005 | Lytle | 607/89 |
| 6,887,260 B1 | 5/2005 | Mcdaniel | 607/88 |
| 6,902,563 B2 | 6/2005 | Wilkens et al. | 606/9 |
| 6,955,672 B2 | 10/2005 | Cense et al. | 606/9 |
| 6,957,905 B1 | 10/2005 | Pritchard et al. | 362/554 |
| 6,976,984 B2 | 12/2005 | Cense et al. | 606/9 |
| 7,029,469 B2 | 4/2006 | Vasily et al. | 606/9 |
| 7,068,910 B2 | 6/2006 | Duine et al. | 385/146 |
| 7,077,544 B2 | 7/2006 | Parker | 607/90 |
| 7,083,610 B1 | 8/2006 | Murray et al. | 606/9 |
| 7,115,123 B2 | 10/2006 | Knowlton et al. | 606/41 |
| 7,118,563 B2 * | 10/2006 | Weckwerth | A61B 18/203 606/13 |
| 7,204,832 B2 | 4/2007 | Altshuler et al. | 606/9 |
| 7,250,045 B2 | 7/2007 | Island et al. | 606/17 |
| 7,250,047 B2 | 7/2007 | Anderson et al. | 606/32 |
| 7,413,567 B2 | 8/2008 | Weckwerth et al. | 606/10 |
| 7,452,356 B2 * | 11/2008 | Grove | A61B 18/203 606/10 |
| 7,762,964 B2 | 7/2010 | Slatkine | 601/7 |
| 7,981,111 B2 | 7/2011 | Grove et al. | 606/27 |
| 8,182,473 B2 * | 5/2012 | Altshuler | A45D 26/0061 606/13 |
| 8,346,347 B2 | 1/2013 | Altshuler et al. | 600/476 |
| 8,551,104 B2 * | 10/2013 | Weckwerth | A61B 18/203 606/89 |
| 8,709,003 B2 | 4/2014 | Island et al. | 606/9 |
| 2001/0023363 A1 | 9/2001 | Harth et al. | 607/90 |
| 2001/0046131 A1 | 11/2001 | Hoelen et al. | 362/231 |
| 2001/0048801 A1 | 12/2001 | Saccomanno et al. | 385/147 |
| 2002/0005475 A1 | 1/2002 | Zenzie | 250/221 |
| 2002/0015430 A1 | 2/2002 | Osmanow et al. | 372/55 |
| 2002/0031160 A1 | 3/2002 | Desor | 372/57 |
| 2002/0049483 A1 | 4/2002 | Knowlton | 607/101 |
| 2002/0091377 A1 | 7/2002 | Anderson et al. | 606/9 |
| 2002/0097587 A1 | 7/2002 | Krietzman et al. | 362/553 |
| 2002/0128635 A1 | 9/2002 | Altshuler et al. | 606/9 |
| 2002/0128695 A1 | 9/2002 | Harth et al. | 607/88 |
| 2002/0151887 A1 | 10/2002 | Stern et al. | 606/41 |
| 2002/0161357 A1 | 10/2002 | Anderson et al. | 606/9 |
| 2002/0161418 A1 | 10/2002 | Wilkens et al. | 607/90 |
| 2002/0173780 A1 | 11/2002 | Altshuler et al. | 606/9 |
| 2002/0173833 A1 | 11/2002 | Korman et al. | 607/88 |
| 2002/0183811 A1 | 12/2002 | Irwin | 607/94 |
| 2003/0004499 A1 | 1/2003 | Mcdaniel | 606/3 |
| 2003/0009158 A1 | 1/2003 | Perricone | 606/9 |
| 2003/0032950 A1 | 2/2003 | Altshuler et al. | 606/9 |
| 2003/0036751 A1 | 2/2003 | Anderson et al. | 606/9 |
| 2003/0046825 A1 | 3/2003 | Slingo | 34/96 |
| 2003/0050561 A1 | 3/2003 | Bazin et al. | 600/476 |
| 2003/0055413 A1 | 3/2003 | Altshuler et al. | 606/9 |
| 2003/0055414 A1 | 3/2003 | Altshuler et al. | 606/9 |
| 2003/0065314 A1 | 4/2003 | Altshuler et al. | 606/9 |
| 2003/0080755 A1 | 5/2003 | Kobayashi | 324/658 |
| 2003/0094714 A1 | 5/2003 | Buazza et al. | 264/1.38 |
| 2003/0105069 A1 | 6/2003 | Robinson et al. | 514/185 |
| 2003/0112623 A1 | 6/2003 | Yu et al. | 362/118 |
| 2003/0133292 A1 | 7/2003 | Mueller et al. | 362/231 |
| 2003/0138249 A1 | 7/2003 | Merola et al. | 396/661 |
| 2003/0146122 A1 | 8/2003 | Westfield et al. | 206/349 |
| 2003/0169400 A1 | 9/2003 | Buazza et al. | 351/159.62 |
| 2003/0177657 A1 | 9/2003 | Andis et al. | 34/96 |
| 2003/0195494 A1 | 10/2003 | Altshuler et al. | 606/9 |
| 2003/0199859 A1 | 10/2003 | Altshuler et al. | 606/9 |
| 2003/0216795 A1 | 11/2003 | Harth et al. | 607/88 |
| 2003/0220633 A1 | 11/2003 | Angeley et al. | 606/18 |
| 2003/0232356 A1 | 12/2003 | Dooley et al. | 435/6.12 |
| 2003/0233138 A1 | 12/2003 | Spooner | 607/93 |
| 2004/0006328 A1 | 1/2004 | Anderson | 604/501 |
| 2004/0010298 A1 | 1/2004 | Altshuler et al. | 607/88 |
| 2004/0010299 A1 | 1/2004 | Tolkoff et al. | 607/88 |
| 2004/0034319 A1 | 2/2004 | Anderson et al. | 604/20 |
| 2004/0034341 A1 | 2/2004 | Altshuler et al. | 606/3 |
| 2004/0036975 A1 | 2/2004 | Slatkine | 359/584 |
| 2004/0046108 A1 | 3/2004 | Spector | 250/227.13 |
| 2004/0054386 A1 | 3/2004 | Martin et al. | 607/88 |
| 2004/0073079 A1 | 4/2004 | Altshuler et al. | 600/1 |
| 2004/0093042 A1 | 5/2004 | Altshuler et al. | 607/88 |
| 2004/0116913 A1 | 6/2004 | Pilcher et al. | 606/9 |
| 2004/0120151 A1 | 6/2004 | Ostler et al. | 362/294 |
| 2004/0122492 A1 | 6/2004 | Harth et al. | 607/88 |
| 2004/0167499 A1 | 8/2004 | Grove et al. | 606/9 |
| 2004/0167500 A1 | 8/2004 | Weckwerth et al. | 606/9 |
| 2004/0167501 A1 | 8/2004 | Island et al. | 606/9 |
| 2004/0167502 A1 | 8/2004 | Weckwerth et al. | 606/9 |
| 2004/0167592 A1 | 8/2004 | Grove et al. | 607/96 |
| 2004/0176754 A1 | 9/2004 | Island et al. | 606/9 |
| 2004/0176823 A1 | 9/2004 | Island et al. | 607/88 |
| 2004/0225339 A1 | 11/2004 | Yaroslavsky et al. | 607/88 |
| 2004/0233655 A1 | 11/2004 | Zimmerman et al. | 362/19 |
| 2004/0241254 A1 | 12/2004 | Kopas et al. | 424/727 |
| 2004/0252940 A1 | 12/2004 | Atac et al. | 385/31 |
| 2005/0008049 A1 | 1/2005 | Oomori et al. | 372/36 |
| 2005/0038418 A1 | 2/2005 | Altshuler et al. | 606/9 |
| 2005/0069566 A1 | 3/2005 | Tamarkin et al. | 424/401 |

(56) References Cited

U.S. PATENT DOCUMENTS

| | | | |
|---|---|---|---|
| 2005/0085878 A1 | 4/2005 | Wilkens et al. | 607/94 |
| 2005/0107849 A1 | 5/2005 | Altshuler et al. | 607/88 |
| 2005/0186168 A1 | 8/2005 | Albin et al. | 424/70.14 |
| 2005/0234527 A1 | 10/2005 | Slatkine | 607/89 |
| 2005/0276072 A1 | 12/2005 | Hayashi et al. | 362/609 |
| 2006/0142750 A1 | 6/2006 | Da Silva et al. | 606/27 |
| 2006/0149343 A1 | 7/2006 | Altshuler et al. | 607/90 |
| 2006/0206103 A1 | 9/2006 | Altshuler et al. | 606/9 |
| 2007/0025947 A1 | 2/2007 | Hansenne et al. | 424/70.22 |
| 2007/0027440 A1 | 2/2007 | Altshuler et al. | 606/9 |
| 2007/0032847 A1 | 2/2007 | Weckwerth et al. | 607/93 |
| 2007/0038206 A1 | 2/2007 | Altshuler et al. | 606/20 |
| 2007/0042020 A1 | 2/2007 | Howard | 424/439 |
| 2007/0060819 A1 | 3/2007 | Altshuler et al. | 600/475 |
| 2007/0129711 A1* | 6/2007 | Altshuler | A45D 26/0061 606/9 |
| 2007/0198004 A1 | 8/2007 | Altshuler et al. | 606/9 |
| 2007/0248590 A1 | 10/2007 | Milne et al. | 424/130.1 |
| 2007/0292461 A1 | 12/2007 | Tamarkin et al. | 424/401 |
| 2007/0299244 A1 | 12/2007 | Chaki et al. | 530/303 |
| 2008/0027518 A1 | 1/2008 | Island et al. | 607/88 |
| 2008/0077198 A1* | 3/2008 | Webb | A61N 5/0618 607/88 |
| 2008/0125834 A1 | 5/2008 | Hendrix et al. | 607/88 |
| 2008/0147053 A1 | 6/2008 | Kang et al. | 606/9 |
| 2009/0043294 A1 | 2/2009 | Island et al. | 606/9 |
| 2009/0270848 A1 | 10/2009 | Weckwerth et al. | 606/9 |
| 2010/0069898 A1 | 3/2010 | O'neil et al. | 606/9 |

FOREIGN PATENT DOCUMENTS

| | | | |
|---|---|---|---|
| DE | 10044662 A1 | 3/2002 | A61K 31/60 |
| DE | 10360503 A1 | 7/2005 | A61K 8/06 |
| EP | 0761257 A2 | 3/1997 | A61B 18/20 |
| EP | 0933096 A2 | 8/1999 | A61B 17/00 |
| EP | 1116476 A2 | 7/2001 | A61B 18/20 |
| EP | 1168535 A1 | 1/2002 | H01S 5/022 |
| EP | 1358872 A1 | 11/2003 | A61K 31/192 |
| FR | 2665366 A1 | 2/1992 | A61N 1/32 |
| FR | 2932679 A1 | 12/2009 | A61K 8/36 |
| JP | 06-273758 A | 9/1994 | G02F 1/1335 |
| JP | 06-334950 A | 12/1994 | H04N 5/74 |
| JP | 11244295 A | 9/1999 | A61B 18/20 |
| JP | 2000300683 A | 10/2000 | A61B 18/20 |
| JP | 2000515410 | 11/2000 | A61B 18/20 |
| JP | 2001252363 A | 9/2001 | A61B 17/00 |
| JP | 2002253573 A | 9/2002 | A61B 18/20 |
| JP | 2003024458 A | 1/2003 | A61N 5/06 |
| JP | 2004136019 A | 5/2004 | A45D 26/00 |
| JP | 2004527330 A | 9/2004 | A61B 17/00 |
| JP | 2004533866 A | 11/2004 | A61B 18/18 |
| JP | 2005278724 A | 10/2005 | A45D 26/00 |
| JP | 2006192073 A | 7/2006 | A61N 5/06 |
| JP | 2006518614 A | 8/2006 | A61B 18/20 |
| JP | 2006525036 A | 11/2006 | A61B 17/00 |
| JP | 2007508243 A | 4/2007 | A61K 31/025 |
| JP | 2009509140 A | 3/2009 | A61B 5/00 |
| JP | 5146517 B2 | 2/2013 | H01L 21/28 |
| WO | 96/14083 A1 | 5/1996 | A23L 1/015 |
| WO | 00/02491 A1 | 1/2000 | A61K 41/00 |
| WO | 02/094116 A1 | 11/2002 | A61B 18/18 |
| WO | 03/001984 A2 | 1/2003 | |
| WO | 03/017824 A2 | 3/2003 | A61B 18/00 |
| WO | 03/043697 | 5/2003 | A61N 5/06 |
| WO | 03/049633 A1 | 6/2003 | A45D 26/00 |
| WO | 2004/010884 A1 | 2/2004 | A61B 18/20 |
| WO | 2004/075731 A2 | 9/2004 | A61B 18/20 |
| WO | 2004/080279 A2 | 9/2004 | A61B 18/20 |
| WO | 2005/063193 A1 | 7/2005 | A61K 8/06 |
| WO | 2007/019536 A2 | 2/2007 | A61B 18/20 |
| WO | 2009/089177 A1 | 7/2009 | A61N 1/00 |

OTHER PUBLICATIONS

Balentine, Douglas A. et al., "The Chemistry of Tea Flavonoids," Critical Reviews in Food Science and Nutrition, vol. 37, No. 8, pp. 693-704 (12 pages total), 1997.

Dufresne, Christiane et al., "A Review of Latest Research Findings on the Health Promotion Properties of Tea," Journal of Nutritional Biochemistry, vol. 12, pp. 404-421 (18 pages total), 2001.

European Search Report, Application No. 09735456.7, 10 pages, dated Sep. 12, 2014.

Japanese Office Action, Applcation No. 2011-506499, 5 pages, dated Nov. 26, 2013.

Brunsting, L, et al., "The Color of the Skin as Analyzed by Spectrophotometric Methods, II. The Role of Pigmentation", Section on Dermatology and Syphilology and the Division of Physics and Biophysical Research, The Mayo Foundation; pp. 575-592, Apr. 29, 1929.

Brunsting, L, et al., The Color of the Skin as Analyzed by Spectrophotometric Methods, III. The Role of Superficial Blook, Section on Dermatology and Syphilology and the Division of Physics and Biophysical Research, The Mayo Foundation; pp. 593-613, Apr. 29, 1929.

Miller, Steve et al., "Isolation and Characterization of Protoporphyrin IX from Bacterial Catalase," The Journal of Biological Chemistry, vol. 235, No. 11, 3 pages, Mar. 7, 1960.

Brown, E.B., "Modern Optics," Radiometry and Photometry, Reinhold Publishing Corporation, 3 pages, 1965.

Cornelius, C.E. et al., "Red Fluorescence of Comedones: Production of Porphyrins by Corynebacterium Acnes," The Journal of Investigative Dermatology, vol. 49(4), PMID: 4228644, [PubMed—Indexed for Medline], 3 pages, Oct. 1967.

Dalton, J. et al., "Reaction Between Molecular Oxygen and Photoexcited Protoporphyrin IX," Nature, vol. 235, 1 pages, Feb. 18, 1972.

Hoeffler, Ulrich, "Enzymatic and Hemolytic Properties of Propionibacterium Acnes and Related Bacteria," Journal of Clinical Microbiology, vol. 6, No. 6, 4 pages, Jun. 10, 1977.

Formanek, I. et al., "Porphyrinsynthesis by Propionibacterium Acnes (author's translation)," Archives for Dermatological Research, vol. 259(2), German, PMID: 334087 [PubMed—indexed for Medline], 9 pages, Aug. 22, 1977.

Lee, W.L. et al., "Comparative Studies of Porphyrin Production in Propionibacterium Acnes and Propionibaceterium Granulosum," Journal of Bacteriology, vol. 133(2), PMID: 637914 [PubMed—Indexed for Medline] 5 pages, Aug. 25, 1977.

Mills, O.H. et al., "Ultraviolet Phototherapy and Photochemotherapy of Acne Vulgaris," Archives of Dermatological Research, , vol. 114(2), PMID: 147054 [PubMed: Indexed for Medline] 3 pages, Feb. 1978.

Fanta, D. et al., "Porphyrinsynthesis of Propionibacterium Acnes in Acne and Seborrhea (author's translation)," Archives of Dermatological Research, vol. 261, German, PMID: 148872 [PubMed—indexed for Medline], 5 pages, Apr. 7, 1978.

McGinley, K.J. et al., "Facial Follicular Porphyrin Fluorescence: Correlation with Age and Density of Propionibacterium Acnes," British Journal of Dermatology, Vo. 102(4), PMID: 7387886 [PubMed—Indexed for Medline] 5 pages, Jul. 24, 1979.

Sliney, D. et al., "Safety with Lasers and Other Optical Sources, A Comprehensive Handbook," Plenum Press, 9 pages, Jul. 1980.

Fanta, D. et al., "Porphyrin Synthesis by Propionibacteria in Dependence of External Factors," Archives of Dermatological Research, vol. 271, 7 pages, Jul. 10, 1980.

Diffey, B. L. "The consistency of studies of ultraviolet erythema in normal human skin." Physics in medicine and biology 27.5, 6 pages, 1982.

Melo, T.B. et al., "In Vivo Porphyrin Fluorescence for Propionibacterium Acnes. A Characterization fo the Fluorescing Pigments," Dermatologica, vol. 164(3), PMID: 7084539 [PubMed—Indexed for Medline] 9 pages, Mar. 1982.

Parrish, J. et al., "Erythema and Melanogenesis Action Spectra of Normal Human Skin," Photochemistry and Photobiology, vol. 36, 5 pages, Mar. 15, 1982.

(56) References Cited

OTHER PUBLICATIONS

Kjeldstad, B. et al., "Influence of pH on Porphyrin Production in Propionibacterium Acnes," Archives of Dermatological Research, vol. 276(6), PMID: 6517611 [PubMed—Indexed for Medline] 5 pages, 1984.
Melo, T.B. et al., "Photodestruction of Propionibacterium Acnes Porphyrins," Z. Naturforsch, vol. 40(C), PMID: 3993179 [PubMed—Indexed for Medline] 4 pages, Oct. 22, 1984.
Kjeldstad, B. et al., "Porphyrin Photosensitization of Bacteria," Adv. Exp. Med. Biol., PMID: 4096295 [PubMed—indexed for Medline], 5 pages, 1985.
Kjeldstad, B. et al., "An Action Spectrum for Blue and Near Ultraviolet Inactivation of Propionibacterium Acnes; with Emphasis on a Possible Porphyrin Photosensitization," Photochemistry and Photobiology, vol. 43(1), PMID: 3952162 [PubMed—Indexed for Medline] 4 pages, Jul. 19, 1985.
Guideline for Limits of Exposure to Ultraviolet Radiation of Wavelengths between 180 nm and 400 nm, Health Physics, vol. 49, No. 2, 10 pages, Aug. 1985.
Meffert, H. et al., "Phototherapy of Acne Vulgaris with the "TuR" UV 10 Body Section Irradiation Unit [translation]," Dermatol. Monatsscher., vol. 172, German, PMID: 2938991 [PubMed—Indexed for Medline] 6 pages, 1986.
Meffert, H. et al., "Phototherapy of Acne Vulgaris with the UVA Irradiation Instrument TBG 400 [translation]," Dermatol. Monatsscher, vol. 172, German, PMID: 2937663 [PubMed—Indexed for Medline] 2 pages, 1986.
Johnsson, A. et al., "Fluorescence from Pilosebaceous Follicles," Archives of Dermatological Research, vol. 279(3), PMID: 3592747 [PubMed—Indexed for Medline] 4 pages, 1987.
Meffert, H. et al., "Treatment of Acne Vulgaris with Visible Light [translation]," Dermatol. Monatsscher, vol. 173, German, PMID: 2963772 [PubMed—Indexed for Medline] 2 pages, 1987.
Meffert, H. et al., "Therapy of Acne with Visible Light. Decreased Irradiation Time by Using a Blue-Light High-Energy Lamp [translation]" Dermatol. Monatsschr., German, PMID: 2150382 [PubMed—Indexed for Medline] 7 pages, 1990.
Kjeldstad, B. et al., "Near-UV-Induced Radicals in Propionibacterium Acnes, Studied by Electron Spin Resonance Spectrometry at 77 K.," Journal of Photochemistry and Photobiology, vol. 9(2), PMID: 1650821 [PubMed—Indexed for Medline] 7 pages, Sep. 21, 1990.
Morys et al., "The Accurate Measurements of Biologically Effective Ultraviolet Radiation," International Symposium on High Latitude Optics, 10 pages, Jul. 1993.
Webster, G.F., "Inflammation in Acne Vulgaris," Journal of the American Academy of Dermatology, vol. 33(2 Pt. 1), Review, PMID: 7622652 [PubMed—Indexed for Medline] 7 pages, Aug. 1995.
Leung, S., "The Porphyrin Page," website at http://www.washburn.edu-cas-chemistry-sleung-porphyrin/page.html, Created Apr. 16, 1996, Last Modified Nov. 11, 2002, printed Jun. 22, 2004, 7 pages.
Arakane, K. et al., "Singlet Oxygen (1 delta g) Generation from Coproporphyrin in Propionibacterium Acnes on Irradiation," Biochemical and Biophysical Research Communication, vol. 223, Article No. 0937, PMID: 8687438 [PubMed—Indexed for Medline], 6 pages, Jun. 25, 1996.
Sigurdsson, V. et al., "Phototherapy of Acne Vulgaris with Visible Light," Dermatology, vol. 194(3), PMID: 9187844 [PubMed—Indexed for Medline] 5 pages, Nov. 15, 1996.
Predicate Devices: LightSheer Diode Laser System by Star Medical/Coherent Star, K973324, K982940, K001746, 1997.
Leyden, J., "Therapy for Acne Vulgaris," The New England Journal of Medicine, vol. 336, No. 16, Massachussetts Medical Society, 7 pages, Apr. 17, 1997.
UV Index definition, Canadian Environmental Web page, See entire document, 3 pages, Jun. 1, 1998.
Karu, Tiina, "Primary and Secondary Mechanisms of Action of Visible to Near-IR Radiation on Cells," Journal of Photochemistry and Photobiology, vol. 49, 17 pages, Nov. 9, 1998.
Saiki, Hiroyasu et al., "Diffusion of Porphyrins and Quinones in Organic Solvents," Phys. Chem. Chem Phys., vol. 1, 4 pages, 1999.
Code of Federal Regulations, Class I Accessible Emmission Limits for Laser Radiation, Food and Drug Administration, HHS, 2 pages, Apr. 1, 1999.
Yoo, Yeong-Min et al., "Hemoglobin Toxicity in Experimental Bacterial Peritonitis Is Due to Production of Reactive Oxygen Species," Clinical and Diagnostic Laboratory Immunology, vol. 6, No. 6, 2 pages, Jul. 12, 1999.
IEC Technical Report 60825-8, "Safety of Laser Products—Guide for the Safe Use of Medical Laser Equipment," 6 pages, Nov. 1999.
Papageorgiou, P. et al., "Phototherapy with Blue (415 nm) and Red (660 nm) Light in the Treatment of Acne Vulgaris," British Journal of Dermatology, vol. 142(5), PMID: 10809858 [PubMed—indexed for Medline] 6 pages, Dec. 7, 1999.
Angelopoulou, E., "The Reflectance Spectrum of Human Skin", Dept. of Computer & Information Science, Technical Reports (CIS), University of Pennsylvania; 14 pages, Dec. 20, 1999.
Romiti, R. et al., "High-Performance Liquid Chromatography Analysis of Porphyrins in Propionibacterium Acnes," Archives of Dermatological Research, vol. 292(6), PMID: 10929774 [PubMed—Indexed for Medline] 3 pages, Jan. 7, 2000.
Bagdonas, Saulius et al., "Phototransformations of 5-Aminolevulinic Acid-Induced Protoporphyrin IX in Vitro: A Spectroscopic Study," Photochemistry and Photobiology, vol. 72(2), 7 pages, May 6, 2000.
Shalita, A. et al., "Acne Photoclearing (APC) Using a Novel, High-Intensity, Enhanced, Narrow-Band, Blue Light Source," Clinical Application Notes, vol. 9(1), ESC Medical Systems Ltd., PB 558-0230, Rev. A, 4 pages, 2001.
International Standard IEC 60825.1, Safety of Laser Products—Part 1: Equipment Classification, Requirements and User's Guide, Editon 1.2, 121 pages, 2001.
Koval'skaya, N.E. et al., "The Efficiency of the Formation of Singlet Oxygen by a Sensitizer Based on Zinc Phthlocyanine," Journal of Applied Spectroscopy, vol. 68, No. 2, 4 pages, 2001.
Buchczyk, Darius P. et al., "High Efficiency of 5-Aminolevulinate-Photodynamic Treatment Using UVA Irradiation," Carcinogenesis, vol. 22, No. 6, 5 pages, 2001.
Mason, Maria G. et al., "Extracellular Heme Peroxidases in Actinomycetes: a Case of Mistaken Identity," Applied and Environmental Microbiology, vol. 67, No. 10, 8 pages, Jul. 18, 2001.
Jappe, U. et al., "Propionibacterium Acnes and Inflammation in Acne; P. Acnes has T-Cell Mitogenic Activity," British Journal of Dermatology, vol. 146, 8 pages, Sep. 12, 2001.
Kawada, A. et al., "Acne Phototherapy with a High-Intensity, Enhanced, Narrow-Band, Blue Light Source: An Open Study and In Vitro Investigation," Journal of Dermatological Science, vol. 30(2), PMID: 12413768 [PubMed—indexed for Medline] 7 pages, Jun. 19, 2002.
Ashkenazi, H. et al., "Eradication of Propionibacterium Acnes by its Endogenic Porphyrins after Illumination with High Intensity Blue Light," FEMS Immunology and Medical Microbiology, vol. 35(1), PMID: 12589953 [PubMed: Indexed for MedLine], 8 pages, Jul. 24, 2002.
Harnessing Light to Treat Stretch Marks and Other Hypopigmented Scars, Skin & Aging, Supplement to Nov. 2002 Skin & Aging.
Elman et al., "The Effective Treatment of Acne Vulgaris by a High-Intensity, Narrow Band 405-420 nm Light Source," Journal of Cosmetic & Laser Therapy, vol. 5, 6 pages, Nov. 27, 2002.
Hode, L., "Are Lasers More Dangerous than IPL Instruments?," Lasers in Surgery and Medicine, Supplement 15, 3 pages, 2003.
Wagener, Frank et al., "Different Faces of the Heme-Heme Oxygenase System in Inflammation," Pharmaceutical Reviews, vol. 55, No. 3, The American Society for Pharmacology and Experimental Therapeutics, 21 pages, 2003.
U.S. Appl. No. 60/450,243, by Robert E. Grove, entitled "Method and Apparatus for the Treatment of Benign Pigmented Lesions", 12 pages, filed Feb. 25, 2003.
U.S. Appl. No. 60/450,598, by Robert E. Grove, entitled "Personal Light Based Acne Treatment Device and Method", filed Feb. 26, 2003.

(56) References Cited

OTHER PUBLICATIONS

U.S. Appl. No. 60/451,091, by Robert E. Grove, entitled "Method and Device for Handheld and Cordless Light-Based Epilation", 6 pages, filed Feb. 28, 2003.
U.S. Appl. No. 60/452,304, by Robert E. Grove, entitled "Optical Sensor and Method for Identifying the Presence of Skin", 8 pages, filed Mar. 4, 2003.
U.S. Appl. No. 60/451,981, by Robert E. Grove, entitled "Method and Apparatus for the Repigmentation of Human Skin", 7 pages, filed Mar. 4, 2003.
U.S. Appl. No. 60/452,591, by Robert E. Grove, entitled "Method and Device for Sensing Skin Contact", 7 pages, filed Mar. 6, 2003.
U.S. Appl. No. 60/456,379, by Robert E. Grove, entitled "Apparatus and Method for the Radiative Treatment of Skin with Increased Eye Safety", 5 pages, filed Mar. 20, 2003.
U.S. Appl. No. 60/456,586, by Robert E. Grove, entitled "Handheld Dermatological Treatment Device with Power Meter", 5 pages, filed Mar. 21, 2003.
U.S. Appl. No. 60/458,861, by Robert E. Grove, entitled "Method and Apparatus for Dermatologic Treatment Utilizing Battery-Powered Laser Diode Bars", 11 pages, filed Mar. 27, 2003.
Anonymous, "Akne-Guidelines Schweiz," [Online], Martin Pletscher: Dermatologie, Retrieved from Internet: http://www.martinpletscher.ch/dermatologie/akne.html, 5 pages, May 15, 2003.
U.S. Appl. No. 60/472,056, by Robert E. Grove, entitled "Apparatus and Method for Dermatologic Treatment", 8 pages, filed May 20, 2003.
Burkhart, Craig N. et al., "Assessment of Etiologic Agents in Acne Pathogenesis," Review, Department of Microbiology and Immunology, and Dermatology, Medical College of Ohio at Toledo, 7 pages, Jul. 2003.
Micro Touch Trimmer website, www.asseenontvwork.com/vcc/ideavillage/microtouch/104917, printed Dec. 4, 2003, 21 pages.
Charakida, A. et al., "Phototherapy in the Treatment of Acne Vulgaris," American Journal of Clinical Dermatology, vol. 5(4), Adis. Data Information, 6 pages, 2004.
Elman, M. et al., "Light Therapy in the Treatment of Acne Vulgaris," Dermatological Surgery, vol. 30(2), Dermatology and Lasers Clinic, Tel Aviv and Caesarea, Israel, American Society for Dermatology Surgery, 8 pages, Feb. 2004.
U.S. Appl. No. 10/794,676, by Mark V. Weckworth et al. entitled "Method and Apparatus for the Repigmentation of Human Skin" filed Mar. 3, 2004.
Elman, M. et al., "The Role of Pulsed Light and Hear Energy (LHE) in Acne Clearance," Journal of Cosmetic Laser Therapy, vol. 6, 5 pages, Apr. 1, 2004.
Omi, Tokuya et al., "420 nm Intense Continuous Light Therapy for Acne," Journal of Cosmetic Laser Therapy, vol. 6, 7 pages, Aug. 12, 2004.
Krautheim, A. et al., "Acne: Topical Treatment," Clinics in Dermatology, vol. 22, No. 5, XP004647111, 10 pages, Sep. 1, 2004.
Ross, Victor E., "Optical Treatment for Acne," Dermatologic Therapy, vol. 18, ISSN 1396-0296, 14 pages, 2005.
Ross, Victor E., "Acne, Lasers, and Light," Advances in Dermatology, vol. 21, 29 pages, 2005.
Ortiz, Arisa et al., "A Review of Lasers and Light Sources in the Treatment of Acne Vulgaris," Journal of Cosmetic and Laser Therapy, vol. 7, 7 pages, Mar. 7, 2005.
Hamblin, M. et al., "Helicobacter Phylori Accumulates Photoactive Porphyrins and Is Killed by Visible Light," Antimicrobial Agents and Chemotherapy, vol. 49, No. 7, American Society for Microbiology, 6 pages, Mar. 7, 2005.
Mariwalla, Kavita et al., "Use of Lasers and Light-Based Therapies for Treatment of Acne Vulgaris," Lasers in Surgery and Medicine, vol. 37, 10 pages, Oct. 12, 2005.
Mariwalla, Kavita et al., "Non-Traditional Acne Therapy: The Use of Lasers and Light-Based Therapies," US Dermatology Review 2006, 4 pages, 2006.
Tremblay, J.F. et al., "Light-Emitting Diode 415 nm in the Treatment of Inflammatory Acne: An Open-Label, Multicentric, Pilot Investigation," Journal of Cosmetic and Laser Therapy, vol. 8, 3 pages, Jan. 25, 2006.
Goldberg, David J. et al., "Combination Blue (415 nm) and red (633 nm) LED Phototherapy in the Treatment of Mild to Severe Acne Vulgaris," Jornal of Cosmetic and Laser Therapy, vol. 8, 5 pages, Mar. 29, 2006.
Lee, Seung Yoon et al., "Blue and Red Light Combination LED Phototherapy for Acne Vulgaris in Patients with Skin Phototype IV," Lasers in Surgery and Medicine, vol. 39, 9 pages, Nov. 16, 2006.
Nestor, M., "The Use of Photodynamic Therapy for Treatment of Acne Vulgaris," Dermatologic Clinics, vol. 25, 11 pages, 2007.
"Light Dose Ranging Study of Photodynamic Therapy (PDT) with Levulan + Blue Light in Severe Facial Acne," DUSA Pharmaceuticals, Inc., http://clinicaltrials.gov/ct2/show/NCT00706433, 25 pages, Mar. 2007.
Anonymous, "BlueLight Acne Treatments," [Online], Retrieved from Internet: http://www.topdocs.com/display_procedure.php?id=bluelight, 2 pages, Apr. 10, 2008.
"Comparison of Claro to Other Dermatological Devices for Acne Treatment," Quantitative Assessment of Light Illumination on Organism Reduction; Subculture agar: TSA + 5% Sheep's Blood (Blood agar) Organism Diluent: Butterfield's Buffer or 0.85% Saline; Propionibacterium Acnes (ATCC 11827), 16 pages, Jun. 23, 2008.
Anonymous, "Vi Derm Product Line," [Online], Kalil Medical Products, Retrieved from Internet: http://www.kalilmedical.com/doctor/vi_derm_products.asp, 4 pages, Mar. 2, 2010.
Supplemental European Search Report, Application No. 04712911.9, 3 pages, dated Jun. 12, 2010.
International Search Report, Application No. PCT/US2009/056961, 7 pages, dated Jun. 29, 2010.
Supplemental European Search Report, Application No. 04712922.6, 3 pages, dated Jul. 12, 2010.
European Office Action, Application No. 04714604.8, 5 pages, dated Nov. 16, 2010.
European Office Action, Application No. 04712910.1, 6 pages, dated Nov. 16, 2010.
International Preliminary Report on Patentability, PCT/US2009/056961, 11 pages, dated Mar. 22, 2011.
International Preliminary Report on Patentability, PCT/US2009/057204, 8 pages, dated Mar. 22, 2011.
Supplementary European Search Report, Application No. 09815144, 9 pages, dated Feb. 10, 2012.
European Office Action, Application No. 09815144.2, 6 pages, dated Oct. 10, 2012.
European Search Report, Application No. 08797565.2, 6 pages, dated Oct. 29, 2012.
Japanese Office Action, Application No. 2010-520342, 6 pages, dated Mar. 7, 2013.
European Office Action, Application No. 09815144.2, 5 pages, dated Apr. 3, 2013.
Extended European Search Report, Application No. 13159309.7, 7 pages, dated May 7, 2013.
Japanese Office Action, Application No. 2009-261364, 7 pages, dated Jun. 18, 2013.
Shnitkind, E. et al., "Anti-Inflammatory Properties of Narrow Band Blue Light," Poster Presentation (Conference Unknown), 1 page.
Predicate Devices: SLP 1000 (LC 100) Diode Laser of Palomar Medical Technologies, K010580, K011747.
Predicate Devices: Apex 800 Pulsed Diode Laser of IRIDEX Corporation, K020849.
Predicate Devices: FI Pulsed Diode Laser of Opus Medical, Inc., K030235.
Predicate Devices: LightSheer Diode Laser System manufactured by Lumenis, Ltd.
Predicate Devices: Quantum Flash Lamp System Manufactured by Lumenis, Ltd.
Predicate Devices: CoolGlide Excel YAG Laser by Altus, Inc.
Predicate Devices: Devices by Ya-Man Ltd., of Tokyo, Japan.
Predicate Devices: Oriel Instruments Model 48010, by Spectra-Physics, Stratford, CT.

(56) References Cited

OTHER PUBLICATIONS

Predicate Devices: Panasonic part No. P-170SCW, or HHR300SCP Ni-MH Rechargables, Panasonic P-170SCRP NiCd, by Panasonic Matsushita Electric Corporation of America, Secaucus, NJ.
Predicate Devices: Laser Diode Bar Packages, Part No. ASM06C040W08010B80, Cutting Edge Optronics, of St. Charles, MO.
Predicate Devices: Part No. HX8-101 or FAN-101, or CP 0.8-31-06L, from Melcor.
Predicate Devices: PIC18LF452, manufactured by Microchip Technologies of Chandler, AZ.
Predicate Devices: Transistors IRL3716 (International Rectifier Corp., El Segundo, CA).
Palomar Super Long Pulse Diode Laser System, Clinical Data, Palomar Medical Technologies brochure.
Japanese Office Action, Application No. 2011-527040, 14 pages, dated Feb. 12, 2014.
U.S. Final Office Action, U.S. Appl. No. 12/430,730, 25 pages, filed Sep. 14, 2016.
U.S. Non-Final Office Action, U.S. Appl. No. 14/171,592, 39 pages, filed Nov. 23, 2016.

\* cited by examiner

PHOTOTHERAPY DEVICE THERMAL CONTROL APPARATUS AND METHOD

CROSS-REFERENCE TO RELATED APPLICATIONS

This application is a Continuation of U.S. patent application Ser. No. 11/545,963 filed Oct. 10, 2006, which is a Continuation of U.S. patent application Ser. No. 10/783,607 filed Feb. 19, 2004, now U.S. Pat. No. 7,118,563 issued on Oct. 10, 2006, which claims the benefit of U.S. Provisional Patent Applications No. 60/450,243 filed Feb. 25, 2003; U.S. Provisional Patent Applications No. 60/450,598 filed Feb. 26, 2003; U.S. Provisional Patent Applications No. 60/451,091 filed Feb. 28, 2003; U.S. Provisional Patent Applications No. 60/452,304 filed Mar. 4, 2003; U.S. Provisional Patent Applications No. 60/451,981 filed Mar. 4, 2003; U.S. Provisional Patent Applications No. 60/452,591 filed Mar. 6, 2003; U.S. Provisional Patent Applications No. 60/456,379 filed Mar. 20, 2003; U.S. Provisional Patent Applications No. 60/456,586 filed Mar. 21, 2003; U.S. Provisional Patent Applications No. 60/458,861 filed Mar. 27, 2003 and U.S. Provisional Patent Applications No. 60/472,056 filed May 20, 2003.

BACKGROUND

1. Field of the Invention

The invention relates to a dermatologic treatment apparatus and method, and particularly to a light-based, self-contained, cordless and hand-held apparatus.

2. Description of the Related Art

The introduction of specialized lasers for physician-performed epilation in 1996 (and intense-pulsed light, or IPL, sources shortly thereafter) represented the first real advance in the treatment of unwanted hair since the invention of electrolysis in the late 1800's. The use of lasers and flashlamps in these devices has not only proven to be safe and effective, but unlike electrolysis allows for the treatment of multiple hairs at a time, greatly improving coverage rate.

Light-based epilation with lasers is often termed "laser hair removal", although this term is strictly correct only when follicles undergo sufficient thermal damage to permanently prevent the growth of new hairs ("permanent hair reduction"). Procedures that thermally damage follicles to induce a delay in hair regrowth are more accurately described as hair-regrowth inhibition.

Methods and devices for light-based epilation are now widespread and an estimated three million people worldwide have undergone treatment. This represents a very small section of the potential market, largely because of the high cost and inconvenience associated with physician-based procedures and devices. As a result, there is a desire for lower cost, more compact devices that would lower the cost of physician-based treatments and, ultimately, help enable salon and consumer markets. There is also a desire for devices with enhanced eye safety.

The introduction of the LightSheer Diode Laser System by Star Medical in 1997 for hair-regrowth inhibition (and subsequently, for perm anent hair reduction) marked the beginning of one of the most successful aesthetic laser applications for the dermatologist's office. With several thousand systems installed worldwide, the safety and efficacy of these and similar devices that followed have been well established. Other such devices include the SLP 1000 (LC 100) diode laser of Palomar Medical Technologies, the Apex 800 diode laser of IRIDEX Corporation, and the F1 diode laser of Opus Medical, Inc.

The radiant exposure applied to the skin (often referred to as "fluence", expressed in joules per square centimeter) by this class of devices is typically in the 10-40 $J/cm^2$ range at a wavelength of nominally 800 nanometers. It was initially believed that pulse durations in the 5-30 ms range are optimum; however, subsequent studies showed that longer pulses (up to at least several hundred milliseconds) can quite effectively achieve hair-regrowth inhibition, and can also reduce epidermal heating for a given fluence when a heat conduction path is provided (e.g., by incorporating an output window made of sapphire in contact with the skin).

The high efficiency and small size of the semiconductor diode lasers utilized in these devices generally permit the manufacture of compact systems (typically 1-3 cubic feet in volume) and simple 115 VAC operation. However, the systems typically weigh at least 25-100 pounds and sell in the range of $40,000 to $90,000. A much lower cost, truly portable device would make this popular procedure much more widely available.

Lasers and intense light sources have gained increasing acceptance among dermatologists for effective treatment of a wide range of applications, such as hair-regrowth inhibition and permanent hair reduction, removal of tattoos, treatment of birthmarks, and facial resurfacing. It is well understood by medical professionals, however, that such light sources are capable of serious eye damage or blindness. To achieve reasonable efficacy with many light-based dermatologic procedures, such as reduction of unwanted hair or destruction of small blood vessels, the fluence on the skin typically exceeds 1 $J/cm^2$. These devices produce a fluence at the human eye that is much greater than the maximum permissible exposure, causing such devices and the treatments performed with them to be extremely hazardous if not used or conducted properly. These procedures therefore involve the undertaking of adequate safety measures to protect the eyes of not only the patient, but the laser operator and any other personnel that may be in the same area. (See, for example, IEC Technical Report 60825-8, Safety of laser products—Guideline for the safe use of medical laser equipment.) As stated in the IEC report, with some medical lasers the retina may be exposed to an irradiance that is more than 100,000 times higher than the irradiance incident on the skin or cornea, due to the focusing action of the eye.

With proper safety precautions, such as safety goggles and training of personnel, the risk of eye damage can be greatly reduced. As a consequence, reports of eye injuries to either patients or staff are rare in medical settings. However, risk of eye injury is a constant concern.

The safety of a light-based dermatologic device can be increased by incorporation of a contact sensor that enables device operation only when in the sensor is in contact with a surface, such as a person's skin. For example, the light source (laser, light-emitting diode, flashlamp, etc.) can be placed within a housing having a single open end through which the light propagates; a contact sensor at this open end can enable operation of the device only if the housing is placed up against a contacted surface. In this manner light can only propagate into or through the surface against which the device is placed. However, use of any type of sensor added to increase eye safety adds complexity and may, of course, fail. Thus, the ideal dermatologic treatment device and method would not depend on electronic circuitry or user compliance with safety eyewear for safe use.

Thus it is highly desirable that any light-based device intended for medical application be designed to minimize possible eye damage for a given level of output fluence or therapeutic benefit, by increasing the inherent eye safety of the light. Existing laser hair reduction devices, for example, are much more hazardous to the eye than necessary because their output is highly directional and easily focused by the eye. If their output could be made more highly divergent and/or to have reduced spatial coherence, there would be a greatly reduced risk of eye injury, without significant loss of efficacy.

Examples of office-based, light-based systems for dermatological treatment are described in U.S. Pat. Nos. 6,508,813, 6,277,111, 6,197,020, 6,096,029, 5,885,273, 5,824,023, and 4,232,678, and U.S. published application no. 2002/0005475, and published PCT application no. WO 03/049633. The '5475 published application uses a contact sensor for enabling laser pulses only when the handpiece is in good contact with a patient's skin. One problem with application of such a device in a home use, self-care setting is that a small child, or person attempting to treat eye lashes or eye brows with the device, may still inadvertently shine pulses into their eyes and potentially cause permanent damage to their vision. Similar eye-safety problems would be apparent in a home use, self-care application of the devices described in each of the above-mentioned patents.

The '49633 published application addresses the eye-safety issue by providing a diffusing unit. However, that device is far too bulky, complex and expensive for home use. The device includes a substantially non-portable laser floor unit and an extensible handpiece connected by a long beam delivery light guide. In addition, other safety issues exist for this device. For example, a home use, self-care setting may not be equipped to handle the electrical safety issues of a device that draws high current from a wall outlet. Most importantly, however, the invention described in the application addresses enhanced eye safety from a collimated laser beam, convergent laser beam, concentrated multiple laser beams or a fiber guided beam, and from monochromatic sources. In contrast, divergent light sources can be rendered eye safe substantially more easily, as described below in accordance with the present invention.

The '029 and '020 patents describe devices that provide fluences over 100 J/cm$^2$. These fluences are generally too large to be eye-safe and epidermis-safe in use in a self-care setting. Such output fluences are likely to give rise to fluences at the cornea potentially above the Maximum Permissible Exposure (MPE), described in more detail below, and/or may likely cause burning of the epidermal region of the treated skin. Moreover, such fluence levels are not efficiently produced in a self-contained apparatus, such as a hand-held and battery-powered device as is desired for self-care and home use in accordance with an embodiment of the present invention.

Furthermore, the device described in the '029 and '020 patents provides a very small spot size between 2 and 5 millimeters in diameter corresponding to approximately 0.03 to 0.2 square centimeters in area. Such a small spot implies that only one hair is treated at a time, and in fact some sort of visual targeting is almost certainly required to ensure that the spot is indeed over even a single target follicle. Also, a small spot size such as between 0.03 and 0.2 square centimeters implies a very low coverage rate. That is, for a given number of square centimeters of skin containing unwanted hairs to be treated, the smaller the spot size the longer the necessary treatment time. In addition, while a small spot size would appear to be quite advantageous in that a low energy can still generate a high fluence on the skin surface (since fluence is energy divided by area), the fluence at some depth within the skin, e.g., where the target cells are located, is substantially reduced by scattering within the skin. That is, the smaller the spot size, especially below about 0.5 cm$^2$, the more pronounced the effective lessening of fluence at depth relative to fluence at the surface. In short, if one goes to too small a spot such as is described in the '029 and '020 patents, the end result can be either burning of the epidermis (to get enough fluence in the dermis) or very poor efficacy due to inadequate fluence at depth; either of these options is obviously undesirable.

CURRENT STATE OF THE ART

The current state of the art of light-based epilation is well described by considering the two general types of devices on the market. One market segment encompasses devices designed and sold to physicians. Representative products include the LightSheer diode laser system now manufactured by Lumenis Ltd., the SLP-1000 fiber-coupled diode laser by Palomar Medical Technologies Inc., the Quantum flash lamp system manufactured by Lumenis Ltd., and the CoolGlide Excel YAG laser by Altus Inc. The physician devices are characterized by (a) established efficacy as confirmed by FDA clearance, (b) practical coverage rate, (c) high cost, and (d) relatively large size having a physical design where a handpiece is attached to a console, and (e) output fluences representing a severe eye hazard. These devices provide efficacious and practical light-based epilation and generally involve a peak optical power greater than 50 W, output fluence of greater than 10 J/cm$^2$, spot size greater than 0.5 cm$^2$, and a coverage rate greater than 10 cm$^2$/min. Examples of these office-based devices are described in the patent literature cited above, and further examples may be found in other references cited herein.

The other market segment comprises the limited number of consumer light-based epilation devices. It is believed that there are no personal light-based epilators currently on the market in the United States. At present, the most developed market for consumer light-based devices is Asia, and, in particular, Japan, where there are tens of products on the market. The devices by Ya-Man Ltd. of Tokyo are typical of the state of the art for these products in Japan. These consumer devices are characterized by (a) greatly reduced or no efficacy due to low peak power (~1 W or less) and small spot size (~0.1 cm$^2$ or less), (b) slow coverage rate due to the small spot size and involving the targeting of individual hair follicles, (c) low cost, (d) relatively small size having a physical design where a handpiece is attached to a console or corded to a wall power supply, and (e) output fluences exceeding eye safety limits.

The inventors of an embodiment of the present invention have recognized that a method and device that could provide effective and practical epilation in an entirely handheld and cordless device would be desirable. By cordless and hand-held, it is preferably meant that the device is self-contained in operation, and has, for example, a volume less than 1500 cm$^3$ and a weight less than 1 kg. Such a handheld and cordless device would be substantially less cumbersome than console and handpiece devices and allow the operator to much more conveniently position the device into orientations that are required to best treat a desired region of skin. In addition, it allows easy portability, and freedom to perform treatments in the absence of electricity from a wall outlet. In order to be an effective and practical treatment device, peak optical output powers greater than 10 W, output fluences greater than 4 J/cm², spot sizes greater than 0.25 cm², and coverage rates greater than 10 cm²/min may be generally involved.

While other light sources for hair-regrowth inhibition, such as intense pulsed light, and a variety of lasers, are now commercially available to physicians, diode laser systems have proven to be among the most successful. These devices typically incorporate laser diode bars operating at a wavelength of approximately 800 nm. The systems range in peak optical power from about 90 watts to nearly 3,000 watts.

Discrete laser diodes are limited in peak power to roughly one watt. While this low power may be adequate for treating individual hairs (such as the Ya-Man device manufactured in Japan), treatment of multiple hairs at a time for rapid treatment of extended areas requires peak optical powers of roughly 25 watts or more. Thus diode laser bars, rather than discrete diode laser devices, are incorporated into the diode-based office products named above. The success of these hair-regrowth inhibition systems incorporating laser diode bars, used by doctors and nurses in an office setting, has fueled interest in the development of home-use devices. The inconvenience of multiple visits to the doctor's office has also increased interest in devices that can be used safely and privately at home. Ideally, such a consumer device would be compact, inexpensive and battery powered, while incorporating proven laser diode bar technology. Unfortunately, because of the very high current requirement (~40 A) of laser diode bars, it is generally accepted that any such device could not be powered by batteries, but rather by an electrical cord to a wall outlet.

Examples of other dermatologic devices are described at U.S. Pat. No. 6,533,775, and at U.S. published patent applications no. 2003/0004499 and 2002/0097587, and in other references incorporated by reference above and below herein.

Although potentially eye-safe, the U.S. Pat. No. 6,533,775 patent describes a mechanical hair removal device, and not a light-based hair-regrowth-inhibition apparatus. The device described in the '775 patent includes a light source that reacts chemically with skin cream applied to the surface in order to reduce the onset time. The light produced by the mechanical hair removal device is not for effecting thermal damage of hair follicles to inhibit regrowth. The light is not designed to penetrate through the cream to create any thermal injury to targets within the dermis.

The '97587 application describes a device with variable current control. This device is not designed for medical applications. The reference also does not provide any output fluences, wavelengths or pulse lengths that might by chance render the fluence at the eye of a person to be under the MPE. There would simply have to be many modifications made to this device to render it eye-safe for home use and to render it efficacious for dermatologic treatment for hair-regrowth inhibition.

The '4499 application describes a device that is described as being designed to inhibit hair regrowth. The '4499 application refers to its procedure as bio-stimulation to produce bio-inhibition, and in any case, it is non-thermal. This is a wholly separate field from hair-regrowth-inhibiting devices that operate by causing thermal damage to hair follicles. The '4499 reference uses much lower fluences (or intensities) than would be efficacious for causing thermal damage to a hair follicle to produce hair-regrowth inhibition.

The design of a handheld device for hair-regrowth inhibition requires clever circuit design, and implementation of a dermatologic treatment device that is efficacious and yet eye-safe requires novel optical design. Therefore it has appeared up to now that the creation of a low-cost, light-based dermatologic treatment device, such as a home-use hair-regrowth-inhibiting device that is effective, compact, battery-powered, and incorporates a diode laser or other light source, is an unachievable goal. However, recent advances in both light technology and microelectronics have made possible the present invention of dermatologic devices that are both efficacious and affordable to the average consumer. In some embodiments, these devices can be sufficiently compact as to be entirely handheld and battery-powered. In other embodiments, these devices can be made to be effective for a variety of dermatologic procedures, and yet eye-safe. They are the objects of the present invention, and are described in more detail below.

SUMMARY OF THE INVENTION

Therefore in view of and in accordance with the above, a dermatologic treatment apparatus is provided that is cordless and sufficiently compact as to be hand-held. A self-contained housing is configured for gripping by a person's hand for cordless manipulation in a dermatologic treatment procedure. A diode laser light source, which may include one or more diode laser bars, and an electrical circuit are contained within the housing. The electrical circuit includes one or more batteries for energizing the light source to produce output light pulses. A light path within the housing includes an aperture through which the output light pulses are propagated out of the housing having properties sufficient for providing efficacious treatment.

In one aspect, the cordless apparatus has a total weight of no more than one kilogram, and occupies no more than 1500 cm³ of volume. In a second aspect, the light pulses have a peak power between 10 watts and 120 watts, and have pulse durations between 10 milliseconds and 1 second. The apparatus produces an output fluence between 4 J/cm² and 100 J/cm². The majority of the energy of a light pulse is contained within the spectral band of 700 nm to 1100 nm. In either case, the electrical circuit includes an electronic control circuit for producing output light pulses. In a further aspect, the light source includes one or more laser diode bars, and the electrical circuit is a direct drive electrical circuit.

In another aspect, the light source includes a diode laser, and the electrical circuit is a direct drive electrical circuit. The light pulses have a peak power between 10 watts and 120 watts, and have pulse durations between 10 milliseconds and 1 second. The apparatus produces an output fluence between 4 J/cm² and 100 J/cm², and the output pulses have a spot size between 0.25 cm² and 5 cm². The majority of the energy of a light pulse is contained within the spectral band of 700 nm to 1100 nm. The light pulses are emitted at a pulse repetition frequency between 0.1 Hz and 2 Hz. The cordless apparatus has a total weight of no more than one kilogram, and occupies of no more than 1500 cm³ of volume.

Any of these aspects and features thereof may be combined together and/or with any of the following features. The dermatologic treatment apparatus may be configured for performing an at least temporary hair-regrowth-inhibition procedure, and/or for treating acne. For treating acne, a majority of the energy of a light pulse is contained within the spectral band of 350 nm to 450 nm or between 1000 nm and 1800 nm, or a combination of both of these ranges. The apparatus may also be configured for treating benign pigmented lesions, for performing vascular, skin texture or wrinkle treatments, or combinations thereof.

The electrical circuit may be a direct drive electrical circuit or may include a supercapacitor for energizing the light source. The direct drive circuit is preferably without a storage capacitor, or transformer, or both. An electronic control circuit of the electrical circuit may include a current limiting circuit, a pulsewidth limiting circuit, and/or a pulse repetition frequency limiting circuit. In addition, the one or more batteries may supply a battery voltage $V_{bat}$, and the electronic control circuit may include one or more field effect transistors (FET's) and a voltage supply, wherein the voltage supply drives the gates of the FET's at a voltage greater than the battery voltage $V_{bat}$.

A contact sensor may be included for permitting light pulses to be propagated from the housing only when substantial contact is made between the contact sensor and the contacted surface, such as a person's skin. Light pulses may be triggered automatically when substantial contact is made between the contact sensor and the contacted surface. The apparatus may also include an audible feedback component.

A hair-regrowth-inhibiting device in accordance with various combinations of the above aspects may include any combination of the following further features. A heatsink may be included for contacting a region of the epidermis of a person undergoing treatment. The heatsink preferably has one or more thermal characteristics that serve to remove heat from the epidermis. The temperature of the heatsink may be below, or at, or above a normal skin temperature, wherein a normal skin temperature is a temperature of the skin when not being treated with the device. The heatsink may include a sapphire output window.

A dermatologic treatment method is also provided for cordlessly treating a person's skin. A self-contained housing assembly of a dermatologic treatment device is gripped in a person's hand. The housing assembly is positioned such that an output window component of the device contacts a region of the epidermis of a same or different person. A diode laser light source is energized with an electrical circuit including one or more batteries and an electronic control circuit, each contained within the housing assembly, to produce output light pulses. The output light pulses generated by the light source are transmitted along a light path within the housing including an aperture through which light pulses are propagated from the housing assembly having properties sufficient for efficacious treatment. The hand-held, dermatologic device is then cordlessly manipulated in a skin treatment procedure. The method may be used with an apparatus according to any of the above aspects or features, and in any of the dermatologic procedures mentioned.

INCORPORATION BY REFERENCE

Figure 1:
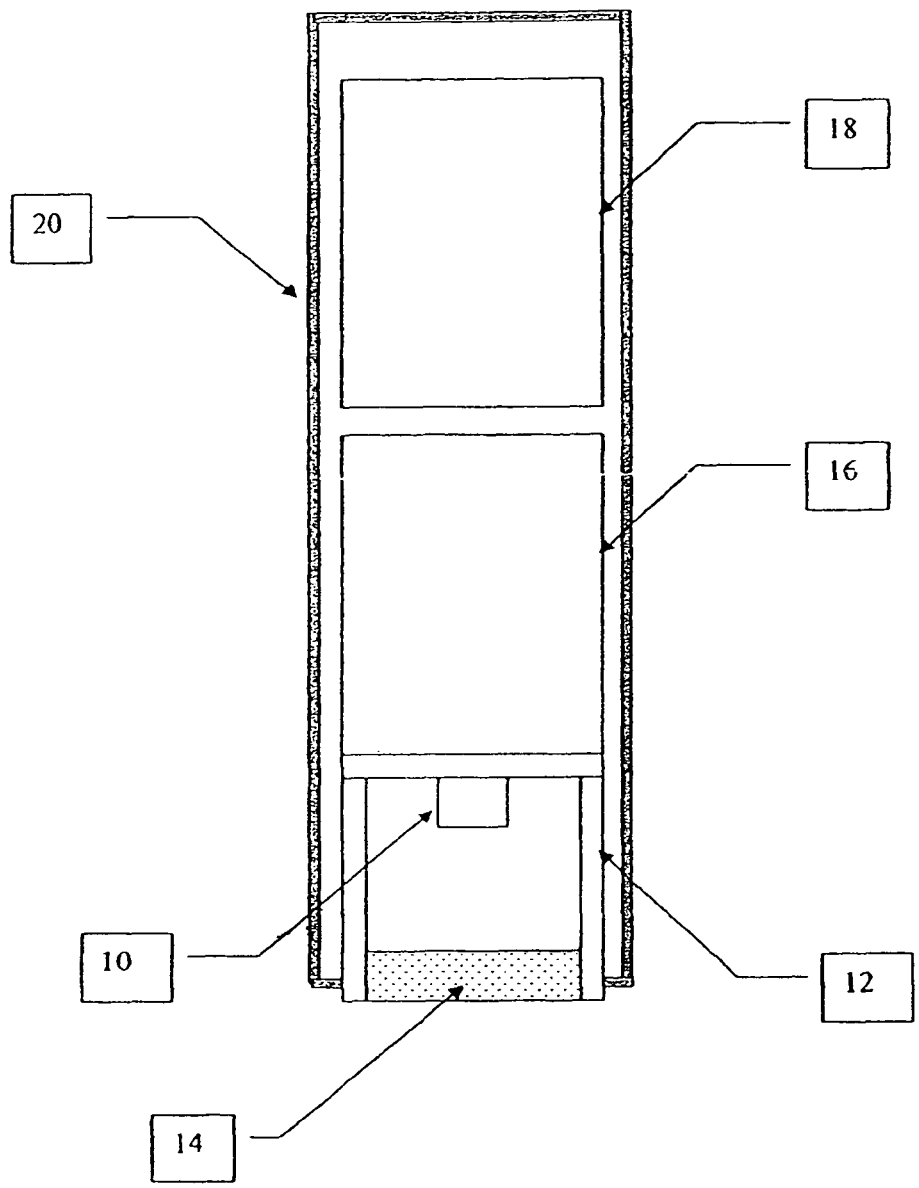
FIG. 1 schematically illustrates a dermatologic treatment apparatus in accordance with a first embodiment that is self-contained and battery-powered.

What follows is a list of citations corresponding to references which are, in addition to those references cited above and below, and including that which is described as background and the invention summary, hereby incorporated by reference into the detailed description of the preferred embodiments below, as disclosing alternative embodiments of elements or features of the preferred embodiments that may not otherwise be set forth in detail below. A single one or a combination of two or more of these references may be consulted to obtain a variation of the elements or features of preferred embodiments described in the detailed description below. Further patent, patent application and non-patent references are cited in the written description and are also incorporated by reference into the preferred embodiment with the same effect as just described with respect to the following references:

U.S. Pat. Nos. 4,232,678, 4,551,628, 4,592,353, 4,690,141, 5,057,104, 5,059,192, 5,075,971, 5,109,465, 5,401,270, 5,405,368, 5,431,647, 5,486,172, 5,700,240, 5,728,090, 5,743,901, 5,820,625, 5,824,023, 5,871,521, 5,885,273, 6,059,765, 6,096,029, 6,138,041, 6,160,831, 6,188,495, 6,197,020, 6,228,074, 6,273,884, 6,277,111, 6,280,438, 6,290,713, 6,440,122, 6,441,943, 6,508,813, 6,511,475, 6,514,242, 6,516,013, 6,517,532, 6,533,775, 6,548,781, 6,563,853 and 6,641,044; United States published applications no. 2003/0233138, 2003/0032950, 2003/0004499, 2002/0128635, 2002/0097587, 2002/0091377, 20020015430, and 2002/0005475; and U.S. provisional patent application No. 60/451,091, filed Feb. 28, 2003; No. 60/456,379, filed Mar. 20, 2003; No. 60/458,861, filed Mar. 27, 2003; No. 60/472,056, filed May 20, 2003; No. 60/450,243, filed Feb. 25, 2003; No. 60/450,598, filed Feb. 26, 2003; No. 60/452,304, filed Mar. 4, 2003;

No. 60/451,981, filed Mar. 4, 2003; No. 60/452,591, filed Mar. 6, 2003; and No. 60/456,586, filed Mar. 21, 2003; and Published PCT applications no. WO 03/049633;

European published application no. EP 1 168 535, EP 0 761 257, EP 1 116 476 and

EP 0 933 096; French patent document no. FR2665366; Japanese patent documents no. JP2000300683, and JP11244295;

German patent document no, DE19629978; and

Sliney, et al., Safety with Lasers and Other Optical Sources, A Comprehensive Handbook, Plenum Press (1980); and Hode, L, "Are lasers more dangerous than IPL instrtrments?" Lasers in Surgery and Medicine, Supplement 15, 2003, p. 6; and poster presentation at corresponding conference.

DETAILED DESCRIPTION OF THE PREFERRED EMBODIMENTS

First Embodiment

A device and method are described in a first embodiment that enable light-based dermatologic treatment with a self-contained and handheld device. The device embodies an advantageous combination of a battery-powered electrical circuit design, a self-contained housing mechanical design, and a light source and optical design, that enables efficacious and practical dermatologic treatment in a cordless and handheld manner.

The light source may be, for example, one or more semiconductor laser diode bars that generate pulses of infrared light. To effect hair-regrowth inhibition, light from the device passes through the epidermis and is absorbed by melanin in the hair shaft and follicle. The resulting brief temperature rise of the follicle temporarily disables it, delaying the regrowth of hair. The device can be pulsed at a repetition rate of up to 0.5 Hz.

Effective dermatologic treatment, e.g., hair-regrowth inhibition, can occur with standard (10-40 $J/cm^2$) output fluences, yet with very long pulse durations (up to 1000 ms). This avoids the need for very high peak laser powers; for example, to produce 20 $J/cm^2$ in 350 ms with a 9 mm by 9 mm output area requires a optical peak power of only 46 watts. The modest peak power requirement, in turn, reduces the electrical pulsed power requirement, and thereby permits battery operation. Through the use of miniature surface-mount electronic components, thermo-electric (TE) modules and advanced nickel-metal-hydride battery technology, such a device has been invented that may be entirely handheld, with the aforementioned parameters in a preferred embodiment.

A device in accordance with a preferred first embodiment is illustrated schematically in FIG. 1. The elements shown are light source 10, mixer 12, output window 14, heat-removal element 16, electrical battery 18, and housing 20. Not shown but involved in the operation of the device are other mechanical, electrical, and optical elements (such as a trigger, drive and control circuitry, sensors, and indicators) such as may be described in more detail below and/or as may be understood by those skilled in the art. That is, FIG. 1 is intended merely to serve to introduce the device of a preferred first embodiment to be described in more detail below.

In operation, the user charges the electrical battery 18 (by placing the device in a charging station, for example, that will provide electrical charge from a wall outlet). Once charged, the user presses an output window 14 or aperture 14 against the surface of the skin to be treated. The aperture or window 14 in contact with the skin is preferably made of sapphire, because of its relatively high thermal conductivity. The output aperture or window 14 may, however, be only an opening or aperture such that the window component 14 that contacts the person's skin may be a frame of the opening. The heat-removal element 16 draws waste heat from light source 10 and may draw heat as well from the skin by conduction through window 14 and mixer 12. The heat-removal element 16 may be a thermoelectric heat exchanger that dissipates heat to the surrounding air by use of a finned heat sink and fan; or may be a solid material that acts as a heat sink due to its high heat capacity (a "thermal battery") as described in some further detail below. The user then activates a pulse from the light source 10 by pressing a trigger button. In an alternative embodiment, the electrical circuit may be designed so that upon sufficiently contacting the skin of a person being treated, a contact sensor located near the output aperture senses sufficient contact of the output window component 14 with a person's skin so that one or more pulses may be automatically activated. The light pulse enters the mixer 12 which serves to distribute the light substantially uniformly onto the output window 14 and ultimately into the skin. The output window 14 is connected to the heat-removal element 16 by mixer 12 and thus additionally serves as a protective heat sink for the skin.

To further simplify operation, the preferred device operates at a fixed, mid-range output fluence setting of nominally 20 $J/cm^2$ and a fixed, mid-range pulse duration of nominally 300-350 ins. In an alternative embodiment, the output fluence would be continuously or discretely adjustable. Details of the electrical circuit design are provided below.

Figure 6:
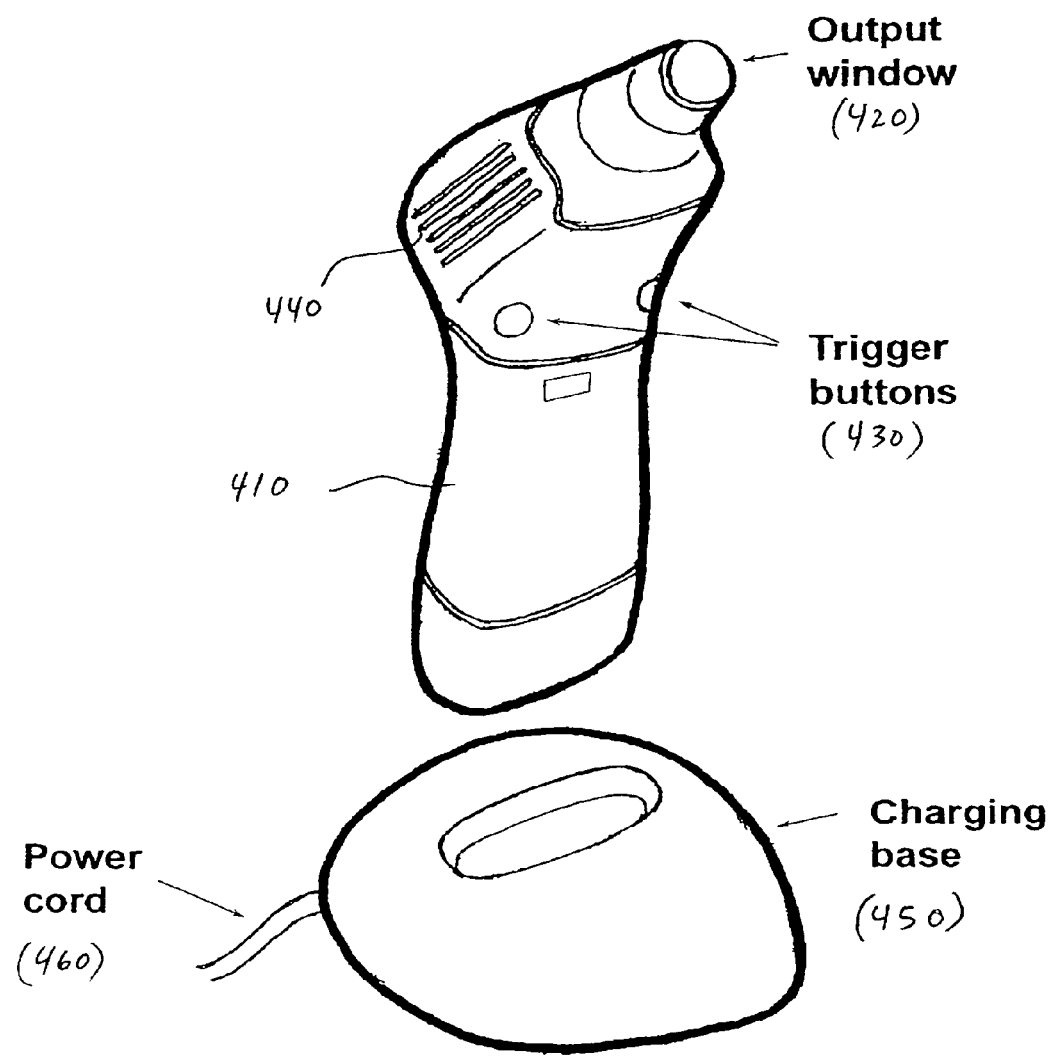
FIG. 6 schematically illustrates a front perspective view of a self-contained housing of a hair-regrowth-inhibiting apparatus in accordance with a preferred embodiment.
Figure 7:
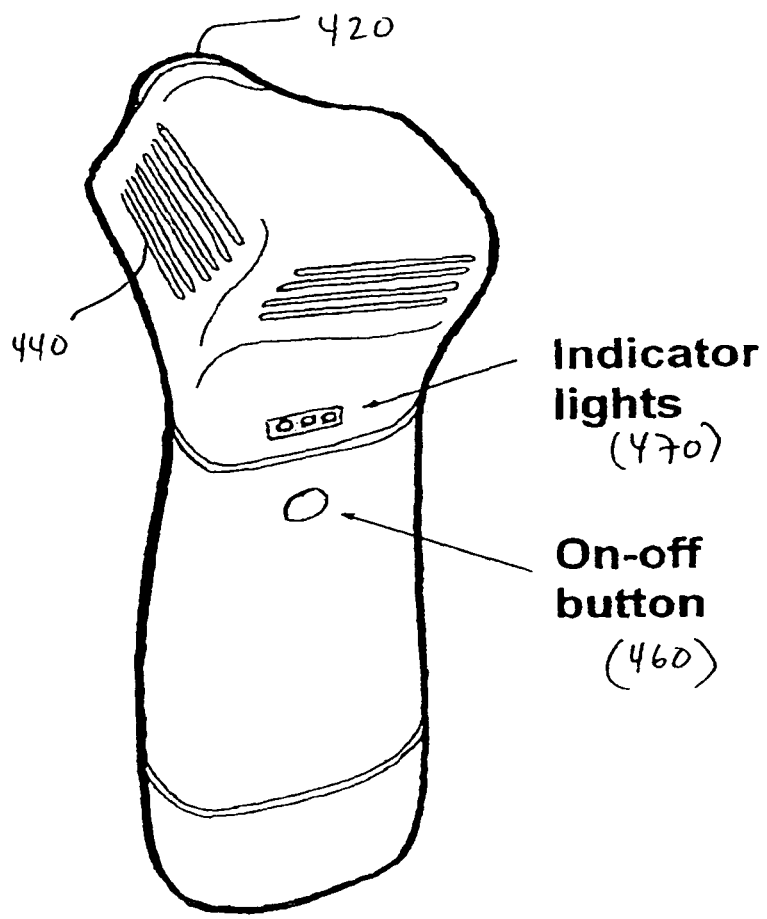
FIG. 7 schematically illustrates a rear perspective view of the self-contained housing of the hair-regrowth-inhibiting apparatus of FIG. 6.
Figure 8:
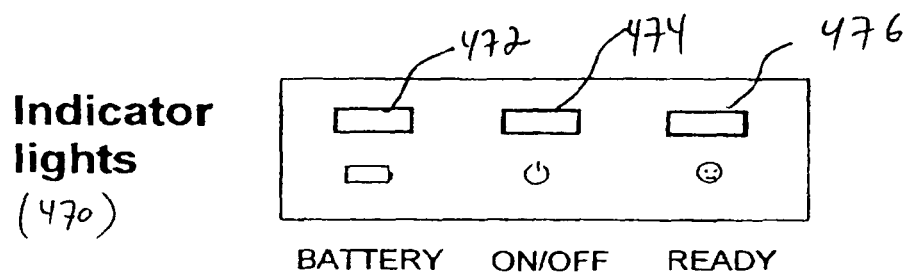
FIG. 8 schematically illustrates indicator lights of the hair-regrowth-inhibiting apparatus of FIGS. 6-7.

Additional details of a preferred embodiment of a light-based hair-regrowth-inhibition apparatus are shown in FIGS. 6-8. The exterior of the unit housing 410 is shown schematically in these figures. FIG. 6 illustrates a perspective front view and the output window 420 is shown. Trigger buttons 430 for initiating laser pulses are also shown and are easily depressed by a left- or right-handed self-care user. Vent louvers or openings 440 are also visible. A charging base 450 is shown with a power cord 460 for recharging the apparatus.

In the rear perspective view of the apparatus shown in FIG. 7, the output window 420 is indicated along with the vent louvers 440, as well as an on-off button 460 and indicator lights 470. The indicator lights 470 are illustrated in more detail in FIG. 8. A battery charge indicator 472, an on/off indicator 474 and a ready indicator 476 are provided examples.

The primary elements of the apparatus will preferably have a volume less than approximately 2000 $cm^3$, and more preferably less than approximately 1000 $cm^3$, and a weight less than approximately one kilogram. Even more preferably, the apparatus may have a volume less than 700 $cm^3$ and a weight less than 700 grams. In this way, the apparatus can be gripped and firmly controlled in a self-care procedure within a user's hand without providing stress in the user's grip and without causing excessive fatigue during use. As illustrated in FIGS. 6-7, the apparatus has a volume of 400 $cm^3$ and a weight of 500 g in a cordless, self-contained device. It is noted that where the term cordless is used herein, it is meant to refer to a unit that is battery-powered and not electrically plugged into an external outlet or power source during use. In addition, where the term self-contained is used herein, it is meant that the unit is not physically connected to a base unit or other such unit and is free to be manipulated without attached wires or couplings. In that sense, a self-contained housing 410 such as that illustrated in FIGS. 6-7 has the light source and batteries contained within it, such that the housing is not attached to any electrical cable or light guide cable that protrudes out of the housing 410. This is not to say that a wireless control, or other wireless coupling, or the charging base 450 cannot be included components of a unit that includes the preferred self-contained housing 410 illustrated in FIGS. 6-7; however in use, the housing 410 is free of externally protruding physical couplings such as control wires, optical cables and power cords.

Even allowing for maximum electrical, thermal, and optical inefficiencies, control circuitry, and mechanical packing factors, the handheld device of the preferred embodiment is highly efficient, self-contained and user friendly. Furthermore, the output parameters of the device establish that it is efficacious and practical in use.

In this section, additional details are provided regarding a preferred method of use of the apparatus. Charging the apparatus involves its placement into a charging base 450 shown in FIG. 6 generally overnight prior to use. Charging of the device is easily done by plugging the power cord into a suitable AC outlet and placing the device into the charging stand 450. Following use, the unit should be returned to the charger 450, so that it will be fully charged for the next use. The unit may be left in the charger 450 for extended periods of time without harm to the unit.

During charging, the left indicator light 472 (FIGS. 7-8) flashes green. When the battery is fully charged, this light will cease flashing and remain green.

Preparing the skin for maximum comfort during use involves shaving the area to be treated prior to treatment, and then wiping with a cool, damp cloth. Because the unit relies on absorption of light by the hair shaft under the skin, the hair should not have been previously removed by plucking or waxing. If either of these methods were performed recently on the area to be treated, treatment should be postponed until hairs are once again visible.

Performing the treatment, after the unit has been fully charged, involves turning on the unit by pressing and releasing the ON-OFF button 460 shown in FIG. 7. When the unit is on, the center indicator light 474 shown in FIG. 8 will illuminate.

For a brief period after the power is turned on, the right indicator light 476 may flash, indicating that the unit is approaching the "ready" state. The right indicator light 476, when steadily green, indicates that the device is ready and will emit a light pulse when either of the two trigger buttons 430 is depressed (provided that the output window 420 is in contact with skin). Two triggers 430 are provided to permit comfortable use of the device in either hand.

To perform the treatment, the output window 420 is placed firmly against the shaved skin area to be treated, and either trigger 430 pressed and released. A beep will be preferably heard when the laser pulse is completed. In a particular embodiment, a beep and/or other tone or sensory indication is preferably heard when good contact is made within the skin indicating that the contact sensors around the window 420 are in contact with the skin and will permit the pulse to be propagated out of the housing 410. Accordingly, the self-care user will know that the unit will not generate a pulse until good contact is established and the tone is heard. In another embodiment, a beep and/or other tone or sensory indication will be heard if after making good contact with the user's skin, the output window 420 is moved away from good contact. This indication is to inform the user that a pulse will not be permitted to be propagated from the housing 410 until good contact is re-established. After the pulse-completed beep is heard, the output window 420 is moved to an adjacent area, allowing for approximately fifty-percent overlap. That is, the tip should be moved a distance about one-half the width of the area contacting the skin. It is not necessary to hold the trigger down throughout the pulse. It is, however, important to maintain full contact between the skin and the output window 420 for the entire duration of the laser pulse. If the output window 420 is lifted from the skin prior to completion of the laser pulse, a distinct tone is sounded to alert the user, and the area should be re-treated with an additional pulse.

The preferred maximum repetition rate of the unit is one pulse every two seconds, and generally between one pulse every second and one pulse every four seconds. Thus there may be a few-seconds delay before the next beep is heard.

All of the various sounds described above serve as audible feedback and aid in the use of the device.

Second and Third Embodiments

Alternative embodiments of a dermatologic treatment device and method incorporate an optical diffuser, described in detail below, to greatly enhance the eye safety of the device while minimally affecting efficacy. The addition of an optical diffuser to increase the divergence and to reduce the spatial coherence of the light emitted from the device allows the apparatus to be classified as a Class I Laser Device under the guidelines of the U.S. Food and Drug Administration Center for Devices and Radiological Health. This permits the use of the apparatus without having to wear laser safety glasses or goggles, and most importantly, eliminates the risk of eye injury if other safety means such as the contact sensor described above should fail.

Accordingly, a device and method for dermatologic treatment are provided in a second and third embodiment that are inherently eye-safe. That is, the device and method are effective in treating various dermatologic conditions (i.e. produce a fluence at the skin surface of greater than about one joule per square centimeter) and yet at the same time, when aimed directly into the eye from any distance, produce a fluence at the human eye that is below the Maximum Permissible Exposure (MPE) as defined by the American National Standards Institute (ANSI) and the International Electrotechnical Commission (IEC). This value for the MPE is essentially the same as the Exposure Limit (EL) published by the International Commission on Non-ionizing Radiation Protection (ICNIRP).

It is recognized in the design of the apparatus that, unlike many applications for lasers and other light sources, dermatologic treatment does not generally require a highly directed beam. As long as the light is confined in some manner within a handpiece or applicator prior to its entering the skin surface, there is very little value in requiring the light to strike the skin at normal incidence (i.e., light rays oriented roughly perpendicular to the skin surface). This is because the skin is a highly scattering medium, and any light rays entering the skin at normal incidence are scattered by epidermal skin cells very near the surface and thus are redirected into all angles. The incorporation of a diffuser accomplishes this spreading of the light rays prior to entering the skin, which has little impact on efficacy but greatly enhances eye safety. It should be noted that simply increasing the divergence of a coherent source such as a laser by inclusion of a simple diverging element (e.g., a lens) is not nearly sufficient to achieve the requisite eye safety, due to the focusing ability of the eye and resulting intensification of that light onto the retina.

It is noted that the devices described in the second and third embodiments below can readily accommodate the essential elements of the first embodiment. That is, the eye-safe devices described in the embodiments below could be realized in a self-contained, battery-powered device. Alternatively, the devices described below could be corded to operate from a conventional wall outlet during use. It is also noted that the method of use of the devices described in the second and third embodiments is essentially the same as that described in the first embodiment.

Figure 2A:
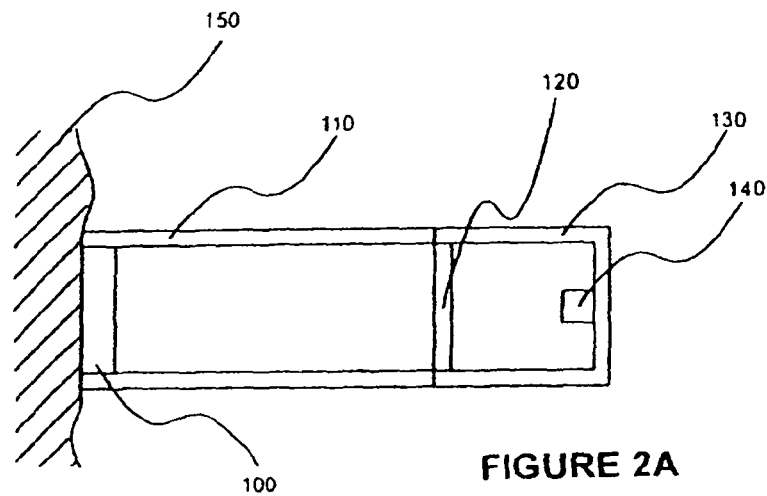
FIG. 2A schematically illustrates a dermatologic treatment apparatus in accordance with a second embodiment in contact with a person's skin, that is eye-safe and that incorporates a transmissive diffuser.

FIG. 2A schematically illustrates a dermatologic device, such as a light-based hair-regrowth-inhibition device, incorporating a transmissive diffuser in accordance with the second embodiment of the invention. When used herein, a transmissive diffuser is intended to describe an element incorporated into a light path having an input surface which the light initially strikes; and a second, output surface from which light propagates. Such input and output surfaces of the transmissive diffuser are separated by the material of the diffuser itself.

The figure schematically illustrates the device, in contact with skin 150, that incorporates the use of a diffusing material 120 through which the light passes before leaving the apparatus though output window (or simply an open aperture) 100. Contained within the source chamber 130 is a light source 140 that emits pulses having many advantageous features. Light source 140 may be, for example, a laser diode assembly for treatment of a dermatological condition, and preferably includes one or two laser diode bars.

The diffusing material 120 is placed over an aperture in source chamber 130. Light source 140 preferably does, but need not, uniformly illuminate diffuser 120. The diffuser 120 is designed to increase the divergence of the light emitted from light source 140, and to reduce the spatial coherence of the light source. Diffuser 120 may be made of a material that scatters light traveling through it, such as an opalized glass substrate. Details regarding appropriate optical diffuser designs and materials are contained in a subsequent section describing component details. In a variation of this embodiment, the inner walls of the source chamber 130 would be coated and/or otherwise constructed of a material that is non-absorbing at the therapeutic wavelengths emitted by source 140. A source chamber that is not substantially non-absorbing would also be acceptable; however, a more intense light source 140 would be involved for the same power delivered to the skin. The requirement for additional power is not desirable, particularly in a cordless, hand-held, self-care device because energy efficiency is at a premium.

The spatial uniformity of the light may be increased through the use of a mixing chamber 110 which may be simply a hollow tube with substantially non-absorbing side walls through which the light would propagate prior to leaving the apparatus through output window 100. If the spatial uniformity of the light at the diffuser is adequate for the desired treatment, the mixer can be omitted, so that the diffuser 120 may even be in contact with the skin and serve as the output window. Alternatively, the diffuser 120 may be located at the position shown in FIG. 2A even if it is determined that sufficient uniformity may be achieved without the function of the mixing chamber 110. It is desired, however, that the diffuser 120 not be placed so close to the light source 140 that substantial non-uniformity results from the light not having sufficiently diverged from the light source before impinging upon the diffuser 120.

Figure 2B:
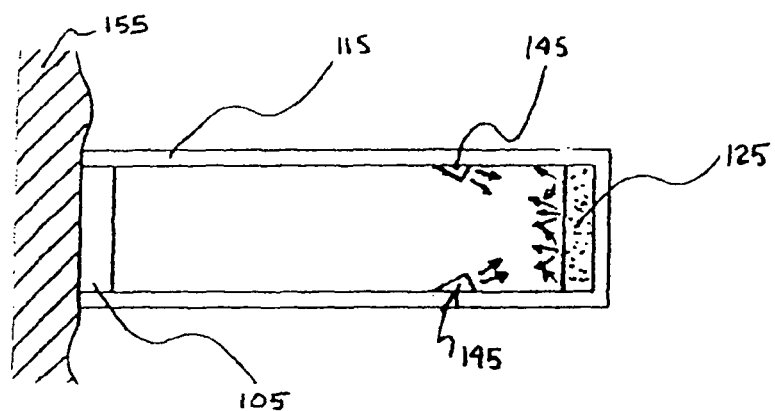
FIG. 2B schematically illustrates a dermatologic treatment apparatus in accordance with a third embodiment in contact with a person's skin, that is eye-safe and that incorporates a reflective diffuser.

FIG. 2B schematically illustrates a dermatologic device, such as a light-based hair-regrowth-inhibition device, incorporating a reflective diffuser in accordance with the third embodiment of the invention. By reference to FIG. 2B, the term reflective diffuser is intended to describe an element incorporated into a light path having a first or input surface which the light initially strikes; however, in contrast to a transmissive diffuser, this first surface also serves as the output surface from which light propagates from the diffuser. It is further noted that the term "reflective" is used in this context to include remitted light. That is, the diffuser may scatter or refract light as well.

In FIG. 2B, a light-based hair-regrowth-inhibition device is illustrated in contact with skin 155 that incorporates the use of a diffusing material 125 which diffuses light from source or sources 145 before the light leaves the apparatus though output window (or simply an open aperture) 105. Contained within the chamber 115 is a light source or sources 145 that emit pulses having many advantageous features. Light source or sources 145 may be, for example, laser diode bars for treatment of a dermatological condition such as unwanted hair.

The diffusing material 125 is placed within chamber 115 in a position generally opposite the skin, as shown. Light source or sources 145 preferably does, but need not, uniformly illuminate diffuser 125. The diffuser 125 is designed to increase the divergence of the light emitted from light source or sources 145 and to reduce the spatial coherence of the light source or sources. Diffuser 125 may be constructed of a highly scattering material such as PTFE, e.g., Teflon. Details regarding appropriate optical diffuser designs and materials are contained in a subsequent section describing component details. In a variation of this embodiment, the inner walls of the chamber 115 would be coated and/or otherwise constructed of a material that is non-absorbing at the therapeutic wavelengths emitted by source or sources 145. The spatial uniformity of the light may be increased through the use of chamber 115 as a mixer which may be simply a hollow tube with substantially non-absorbing side walls through which the light would propagate prior to leaving the apparatus through output window 100. It is further noted that FIG. 2B illustrates the concept of a reflective diffuser in an embodiment wherein light from the source or sources 145 is initially directed away from the skin 155, prior to striking diffuser 125. The device in FIG. 2B could be alternatively constructed wherein light from source or sources 145 initially propagates in a direction toward the skin; but, prior to striking the skin, such light is redirected by a mirror or mirrors back toward the diffuser 125.

Component Design

Light Source

With reference to FIG. 1, the light source 10 is preferably two diode laser bars at a nominal wavelength of approximately 800 nm. Operating specifications may be, for example, 20 J/cm$^2$ output fluence, 350 ms pulse duration, 0.8 cm$^2$ spot size (output aperture), and 0.5 Hz pulse repetition rate. These parameters correspond to an optical peak power of 46 W and a duty cycle of about 18%; the resulting average optical power is thus about 8 W. Diode bars operating at these parameters are about 35-40% efficient; thus the average electrical power into the light source is about 23 W (8 W of emitted average optical power and about 15 W of waste heat). The volume and weight of the light source is about 1 cm³ and 10 g. Alternative embodiments for the light source include use of one diode laser bar rather than two, use of more than two diode laser bars, use of light emitting diodes (LED's), and use of a flash lamp (also known as a flash tube) or arc lamp.

Skin Contact Sensor

To prevent an inadvertent output light pulse from the device when it is not in contact with skin, a skin contact sensor is preferably incorporated into the tip of the preferred dermatologic treatment apparatus. The sensor may include a ring of very small "membrane switches" located around the circumference of the preferred sapphire window. The signals from the membrane switches prevent firing of the device unless it is in substantial contact with a contacted surface such as skin. In an alternative embodiment, the trigger may be eliminated, and the closing of one or more membrane switches may activate one or more light pulses. As described above, audible or other sensory indications are preferably provided when good contact is made, and when the output window is displaced from a good contact position on the user's skin such that firing is disabled until good contact is again established. An audible or other sensory indication is also preferably provided at the end of a pulse indication to provide feedback to the user that the apparatus may be moved to another location before the next pulse.

Charging Base

Between uses of the dermatologic treatment apparatus of the preferred embodiment, it is preferably placed in a charging base (see FIG. 6). The charging base may be similar to those currently produced for use with electric toothbrushes, shavers, phones, etc. The base is connected to a standard AC outlet, and is capable of recharging the batteries overnight.

As mentioned above, the apparatus in the second or third embodiment may also be corded to operate from a standard wall outlet during use, eliminating the need for a charging base.

Mixer in the embodiment shown in FIG. 1, the mixer 12 serves to (a) to mix the light emitted from the diode lasers to produce a uniform beam profile at the output window 14, (b) to provide a low thermal resistance path between the output window 14 and the heat-removal element 16, and (c) to minimize thermal loads on the device that are due to light absorption from back-reflected or back-scattered light.

The mixer 12 comprises a hollow chamber where the wall material is either copper or aluminum. The walls are either the polished substrate or coated to achieve high reflectivity to 800 nm light. The length of the mixer is designed to provide good spatial uniformity of light across the output face. A 1-2 cm length is required to provide adequately uniform illumination on a 1×1 cm output window from two diode bars spaced 6 mm apart. The wall thickness of the mixer is designed to provide good thermal conductivity between the output window 14 and heat removal element 16. For copper walls surrounding a 1×1 cm output window, a wall thickness of about 2 mm is required to conduct about 8 W of average power to a thermal source 2 cm away with a 5 degree C. temperature rise. The volume and weight of the mixer is about 4 cm³ and 20 g. The thermal load on the mixer due to light absorption is less than 1 W. An alternative embodiment of the mixer 12 might include various shapes and may comprise multiple elements to achieve the thermal link between the output window and the heat removal element and to achieve light mixing and low light absorption. The cross-sectional shape may be any of a variety of shapes (such as circular or rectangular) and may vary along the length of the mixer. Because the skin, or the diffuser, or the walls of the mixer may remit light in a direction away from the skin, the mixer may comprise not only low-absorbing side walls, but also a low-absorbing surface opposite the output aperture. Such low-absorbing surface may contain one or more openings through which light from the light source passes, or may simply constitute the surface adjacent to the light source.

In an alternative embodiment, the mixer may consist of an inner mixer, such as a sheet of polished metal, for the purpose of reflecting light from the light source toward the output window 14; and a thicker metal outer surface, such as a copper or aluminum barrel, to conduct heat from output window 14 to heat-removal element 16. In this embodiment, the inner mixer may alternatively be fabricated from a solid transparent material such as glass or acrylic. In this case the light from the light source would be reflected toward the output window 14 by total internal reflection within the glass or acrylic.

Optical Diffuser

The term "diffuser" or "optical diffuser" refers throughout this patent application not only to conventional, commonly known elements such as the "optical disk diffuser" of the flashed opal type (e.g., Oriel Instruments Model 48010, Stratford, Conn.) but more generally to any element that, when incorporated into a light-emitting device having a given radiant exposure or fluence, greatly reduces the integrated radiance ("brightness") of the device. A diffuser generally increases the divergence and reduces the spatial coherence of light incident upon it.

With reference to FIG. 2A, diffuser 120 may be made of a material that scatters light as it travels through it such the abovementioned optical disk diffuser from Oriel. Alternatively, diffuser 120 may be a transparent substrate whose surface has been roughened so as to scatter the incident light through refraction. Diffuser 120 may be a bulk scattering diffuser, made for example from opal glass, PTFE, a thin (e.g. 0.5 mm) sheet of Spectralon, or combinations thereof. The diffuser 120 may alternatively have a refractive or diffractive surface or body; or have a diffusing surface comprising random surface irregularities. Such diffusers may be made of ground glass, sandblasted glass or plastic, or molded materials produced by a randomly textured mold, or combinations thereof. Alternatively, diffuser 120 may have a patterned surface or body, for example with a holographic or Fresnel pattern.

The reflective diffuser 125 as shown in FIG. 2B may be constructed of a highly scattering material such as PTFE, or a commercial material such as Spectralon (available from LabSphere, Inc.). Alternatively, diffuser 125 may comprise a scattering material such as Duraflect (also available from LabSphere, Inc.) applied to the surface of the chamber 115 opposite the skin 155. Alternatively, diffuser 125 may be fabricated simply by roughening the surface of chamber 115 opposite the skin 155; however, the preferred embodiment would incorporate an actual diffusing material such as Spectralon, or an applied surface coating such as Duraflect, due to the low absorption of these materials. Alternatively, diffuser 125 may be made of a material that scatters light as it travels through it such as an opalized glass substrate, e.g., part #48010 manufactured by Spectra-Physics (Oriel), and then backed by a highly reflective mirror; in this way a transmissive diffuser material can be made to serve as a reflective diffuser.

Figure 3A:
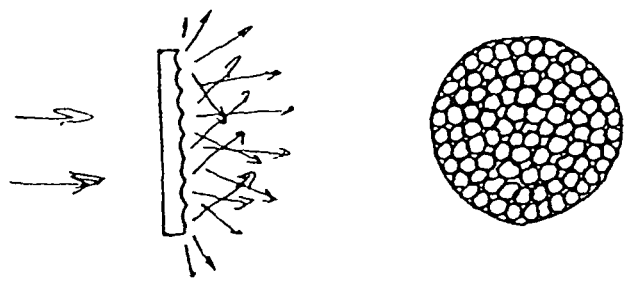
FIGS. 3A and 3B schematically illustrate an optical diffuser in accordance with the second embodiment.
Figure 3B:
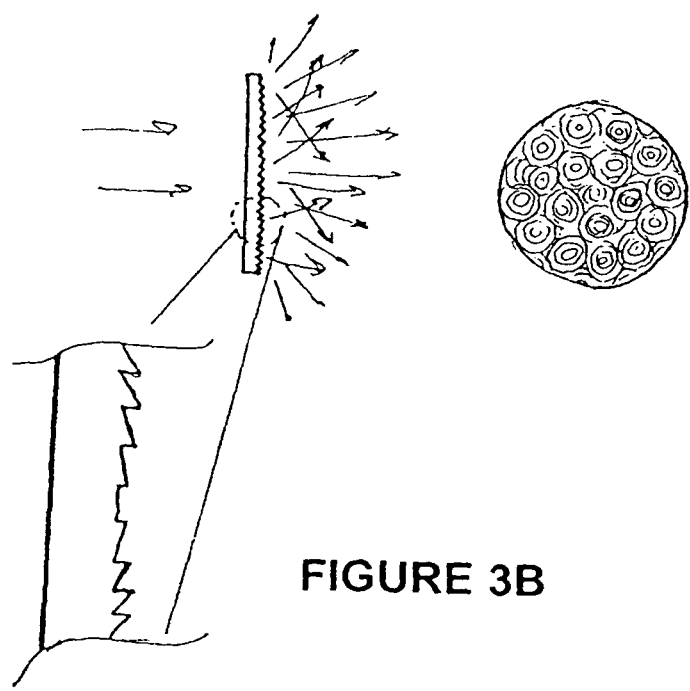

FIG. 3A illustrates an example of a diffuser 120 including transparent screens of the fine-structure or lenticular types. FIG. 3A illustrates transmissive sheets having molded or machined refractive or diffractive elements. The diffuser 120 may also include zones of concentric microgrooves, as illustrated at FIG. 3B.

Figure 3C:
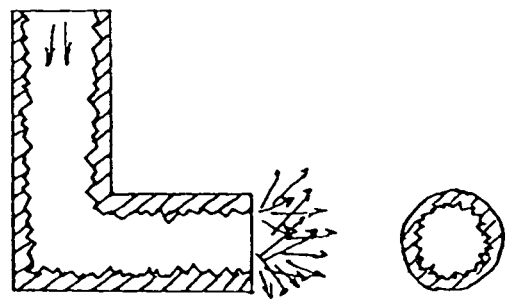
FIG. 3C schematically illustrates an optical diffuser in accordance with the third embodiment.

The diffuser 125 of FIG. 2B may include merely roughened interior surfaces of a passageway through which light is scattered prior to exiting the device, such as illustrated at FIG. 3C, discussed in reference to FIG. 3E in more detail below.

Figure 3D:
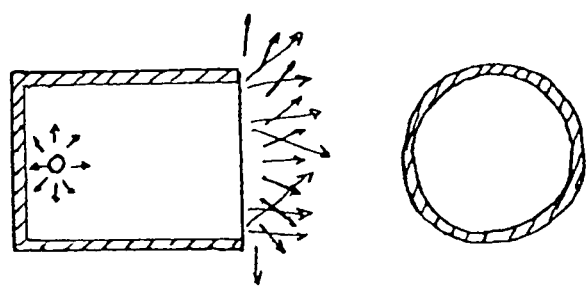
FIG. 3D schematically illustrates yet another type of optical diffuser that has a spatially uniform output.

Yet another means of achieving very low integrated radiance for a given output fluence from a device in accordance with embodiments of the invention includes a small light source approximating a "point source" projecting into a mixer having mirrored walls such as that illustrated at FIG. 3D.

Figure 3E:
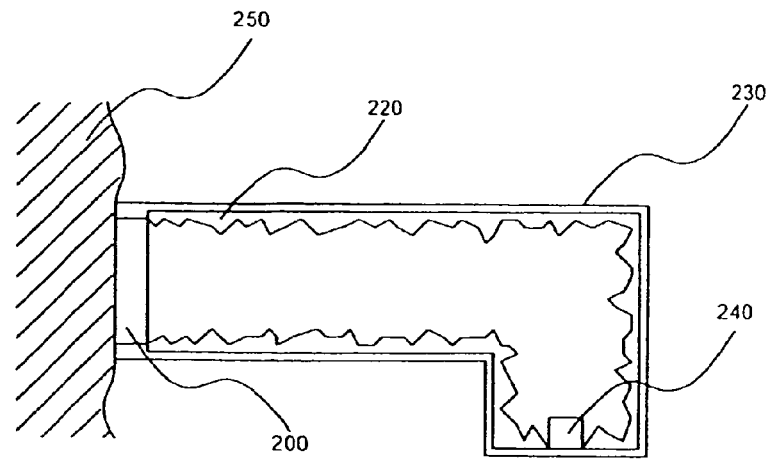
FIG. 3E schematically illustrates the optical diffuser of FIG. 3C in contact with a person's skin during a hair-regrowth-inhibiting procedure or other dermatologic procedure.

FIG. 3E shows an embodiment of the current invention in contact with skin 250 that incorporates the use of the diffusing surface 220 of FIG. 3C which the light strikes before leaving the apparatus though output window 200. Again, light source 240 is housed within source chamber 230. However, instead of a diffusing material through which the light passes prior to leaving the device, a diffusing surface 220 is positioned relative to source 240 such that the light strikes surface 220 prior to leaving the device. Diffusing surface 220 may be merely a roughened surface such as sand-blasted aluminum designed to diffuse the light, or diffusing surface 220 may be a surface coated with a bulk diffuser such as an opalized material used in part #48010 manufactured by Spectra-Physics (Oriel). Surface 220 need not coat the entire inner wall of source chamber 230 but only a sufficient portion to achieve a desired level of beam divergence and reduced spatial coherence. A preferred embodiment would use a material for surface 220 that is substantially non-absorbing at the therapeutic wavelengths emitted by source 240.

Other designs are possible as understood by those skilled in the art and as provided in the literature incorporated by reference herein, i.e., these are merely examples.

Output Window

The output window 14 is preferably a transparent, high heat capacity and high thermal diffusivity material, such as sapphire, with a low thermal resistance connection to the mixer 12. A thickness of 5 mm provides acceptable heat sinking capability for a 1×1 cm sapphire window. The volume and weight of the output window 14 is about 0.5 cm$^3$ and 2 g. The thermal load on the output window is about 8-9 W of average power.

Heat Removal Element

The heat-removal element 16 could be a thermal battery made of a high heat-capacity single-phase material, such as copper, water, or aluminum, or could be any of a variety of phase-change materials such as salt hydrates and paraffin waxes, which can provide 5-10 times greater thermal energy density and thus provide for a more compact thermal battery. An embodiment with the thermal battery material TEAP/Climator ClimSel 24 can store 210 J/cm$^3$ and 144 kJ/kg over a 10 degree C. working range. Thus, for a 10 minute treatment at 23 W of average heat load the thermal battery would be about 70 cm$^3$ and 100 g.

Alternative embodiments of the heat-removal element 16 include a thermoelectric-based heat exchanger. The heat exchanger would have a cold-side heat sink thermally connected to the rest of the device, a thermoelectric module, and a hot-side heat sink thermally connected to the environment. A fan to provide forced convection may be part of this heat exchanger.

Additional Details of a Preferred Second Embodiment

Figure 10:
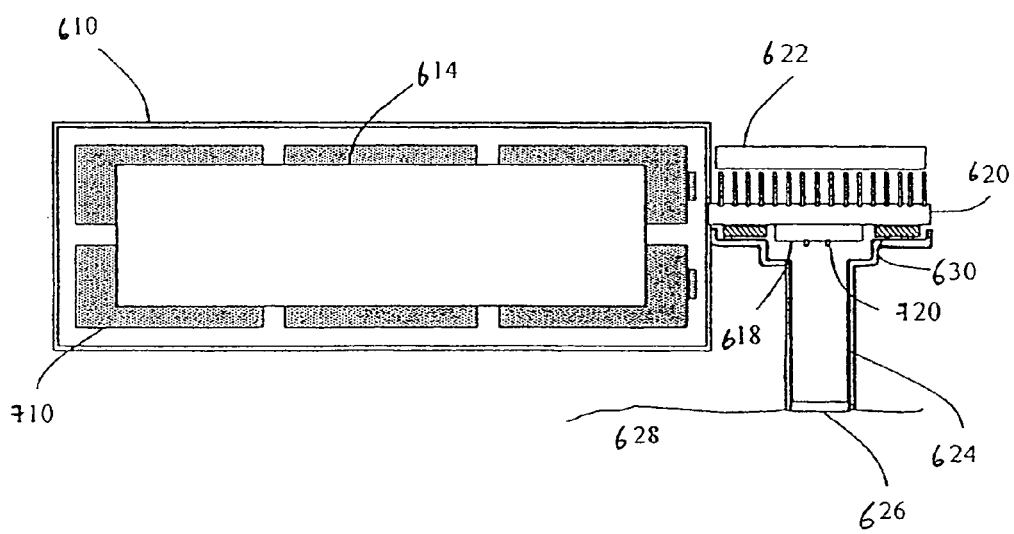
FIG. 10 schematically illustrates a cross-sectional view of a hair-regrowth-inhibiting apparatus in accordance with the second embodiment.

A semi-schematic cross-sectional drawing of an apparatus in accordance with a preferred second embodiment is shown in FIG. 10. Mounted at the end of device housing 610, which also serves as a handle, is the laser head of the device, containing preferably two AlGaAs laser diode bars mounted on a fan-cooled, finned heat sink. The laser light propagates through a square tube having a cross-section of 9 mm by 9 mm, through an opal-glass diffuser and sapphire window pair 626. The sapphire window, which is in contact with the skin during treatment, is held near room temperature by small thermo-electric modules mounted on either side of the diode bars.

Figure 9:
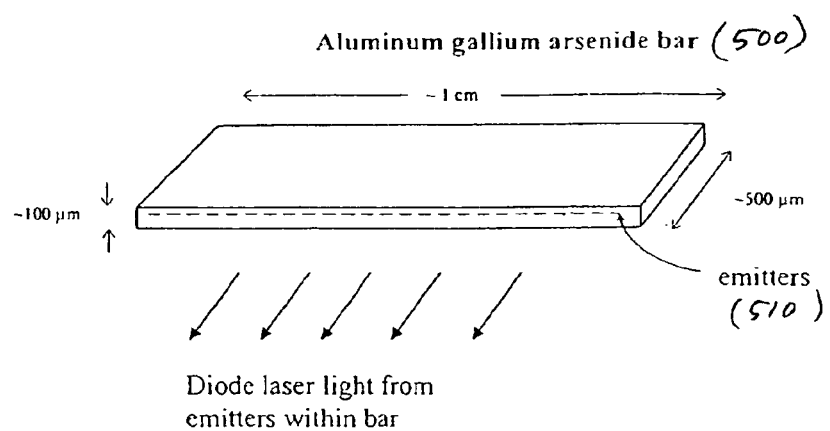
FIG. 9 schematically illustrates a perspective view of an AlGaAs laser diode bar.

A typical diode laser bar 500 including multiple diode emitters 510, such as that illustrated at FIG. 9 (and such as may be manufactured by Spectra-Physics, Inc., of Mountain View, Calif., or Coherent, Inc., of Santa Clara, Calif.), has a continuous optical power output of 20-40 watts, and a maximum peak power output approaching 100 watts. For this reason, a hair-regrowth-inhibition device with an output optical peak power of over 25 W can be designed with only one or two bars 500, rather than 25 or more discrete laser diodes. Each laser diode bar 500 has many individual emitters 510 preferably fabricated on a monolithic structure, and requires roughly 40 amperes of current at a voltage of slightly under 2.0 volts to produce 30 watts of optical peak power output for more than 50 milliseconds.

Device housing 610 contains battery pack 710 consisting of, for example, six nickel-cadmium or nickel-metal-hydride 1.2 V "C size" batteries (e.g., Panasonic part no. P-170SCW, or HHR300SCP). Housing 610 also encloses circuit board 614 containing the control electronics, described in detail below. Electrical power from the battery pack 710 is conditioned and controlled by electronics on circuit board 614, and current of nominally 40 A is conducted through wires (not shown) to laser diode bars 720 mounted on heat sink 618 (e.g., laser diode bar packages, part no, ASM06C040W080810B80, Cutting Edge Optronics).

Heat sink 618 is attached to finned heat sink 620 (e.g., part no. HX8-101, Melcor, Trenton, N.J.), and cooled by fan 622 (e.g., part no. FAN-101 from Melcor) which is also powered by the battery pack 710. Heat sink 618 is preferably a good thermal conductor and an electrical insulator. The material BeO is preferably used for the heat sink 618. The finned heat sink 620 may comprise a block of aluminum or copper or other material of high thermal conductivity. The finned heat sink 620 exchanges heat with the air which is circulated by fan 622. Laser light from laser diode bars 720 passes through mixer 624 (for example, a hollow tube of square cross-section having highly reflective walls, such as gold-plated aluminum).

Light from mixer 624 then passes through diffuser/window 626, preferably of opalized glass (e.g., part no. W13.50 from Swiss Jewel) and sapphire, and subsequently passes into the person's skin 628 containing one or more unwanted hairs. Diffuser/window 626 is prevented from overheating by allowing excess heat from diffuser/window 626 to be conducted through mixer 624 to the cold side of thermo-electric (TE) cooling modules 630 (e.g., Melcor part no, CP 0.8-31-06L). TE modules 630 are in turn cooled by placement of their hot side against heat sink 620. TE modules 630 are preferably solid-state devices that pump heat from mixer 624 to the heat sink 620.

The principal optical axis of the laser diode bars may be aligned with the principal optical axis of the mixer and parallel to the normal to the surface of the diffuser/window 626, as shown in FIG. 10. In an advantageous embodiment, however, the principal optical axis of the light emitted from the laser diode bars is not substantially parallel to the normal of the surface of the diffuser. This may be accomplished by tilting the principal optical axis of the laser diode bars so that they are not parallel to the normal of the surface of the output window; or by mounting the diode bars so that their principal optical axis is parallel to the normal of the surface of the diffuser, but the light emitted from such bars strikes the diffuser at a different angle through the use of a mirror or mirrors. The angle is preferably around 45 degrees. This embodiment permits the light generated by the laser diode bars 720 to already be spreading outward from the forward direction prior to striking the diffuser/window 626, resulting in an even more diffused and eye-safe beam propagated from the housing 410.

Electrical Circuit Design

Laser Diode Circuit Overview

An apparatus and method is described for dermatologic treatment in an embodiment that utilizes battery-powered laser diode bars. The apparatus comprises a hand-held treatment device for dermatologic use, one or more batteries, one or more laser diode bars, and an electronic control circuit. The apparatus enables, for the first time, effective home hair-regrowth inhibition, in a device significantly above the 1 W optical output level that is compact, affordable (less than $1,000) and is free of cords and/or other connections to an electrical outlet. The device incorporates a small number of batteries (preferably three to six), an efficient circuit design that effectively draws 40 amperes or more from the batteries, and typically contains one or two laser diode bars producing a combined optical peak power output of 10-120 W, or more preferably 30-60 W, at 800 nm. With this apparatus, the consumer can inhibit hair regrowth in the privacy of the home using a device that has an output power much higher than existing home "hair removal" devices (enabling more effective hair-regrowth inhibition and a faster coverage rate) while also enjoying the convenience of compact device size and cordless (battery-powered) operation. The device may also be suited for use while plugged in, e.g., when it is not inconvenient to utilize the device while it is attached to an outlet or other source of electrical power. This can save battery power at times and can also serve to recharge the batteries.

The concept is not limited in its advantageous application to hair-regrowth inhibition, nor to the preferred wavelength of approximately 800 nm; but rather, may be applied more broadly to dermatologic treatment utilizing battery-powered laser diode bars for other applications, and/or other wavelengths. For example, benign pigmented lesions and unwanted leg veins may be treated by dermatologists in an office setting using an 800-nm laser diode bar source; and treatment of acne by destruction of the sebaceous gland is possible utilizing a similar laser diode bar source at 1400 or 1700 arm (both absorption peaks of sebum). The invention is also not limited to devices containing only one or two laser diode bars each containing multiple laser diode emitters, but may include a different number of laser diode bars and may include other alternative light sources such as solid-state lasers, semiconductor lasers, VCSEL's and flashlamps, among others that may be understood to those skilled in the art that generally meet the input and output criteria described herein for a battery-powered, home care device.

An apparatus and method in accordance with a preferred embodiment include increased eye safety by increasing the divergence and reducing the spatial coherence of the light emitted from the output aperture of the dermatological apparatus. It is noted that the output aperture may be a clipping aperture, but as used herein, is not so limited, and the term is meant to include any plane through which the light travels or transmits, and may comprise a particular solid material such as a window or optical diffuser or a fluid such as air.

The apparatus and method may alternatively involve operation from a conventional wall outlet, eliminating the need for batteries.

Overview of Batteries and Control Electronics

Although a transformer can in principle be used to increase the 0.001-3 amperes typically drawn from batteries to the 40 ampere level, this approach is impractical in the home device application described for two reasons. First, incorporation of a suitable transformer adds weight, volume and cost; and secondly, a step-up in current via a transformer necessarily is accompanied by a corresponding step-down in voltage. Thus, for example, a transformer that converts 2 A at the input to 40 A and 2 V at the output has a turns ratio of 20:1, and thus utilizes an input voltage of 40 V. Since batteries are typically 1.2-1.5 V output, either many batteries (greater than 25), or voltage boost circuitry would likely be employed. These complexities add further to the weight, size and cost of the device. Alternatively, one might consider the addition of a "supercapacitor" (i.e. a high-capacitance electrical component that has recently become commercially available, termed an UltraCapacitor by Maxwell, Inc. of San Diego, Calif.) with a capacitance of 1 farad or more. This device can provide very high current, but unlike a battery its output voltage decreases rapidly at constant current output, in addition to adding its own weight and volume.

The handle of the preferred apparatus contains a rechargeable battery pack containing five "sub-C" size nickel-metal-hydride or similar batteries, capable of powering the device without a main storage capacitor or transformer for approximately 300-500 pulses between recharges. That is, the circuit of the preferred embodiment is a "direct drive" electrical circuit wherein the current flowing from the batteries during a light pulse is substantially equal to the current flowing through the light source, or is substantially equal to the sum of the currents flowing in parallel through multiple light sources. The voltage provided by the batteries will not be substantially greater than the voltage applied to the light source due to small voltage drops at various resistances in the circuit.

The electrical battery serves as the source of electrical power in a preferred embodiment. The electrical battery could be comprised of (a) a battery that drives the light source directly, which is the preferred direct-drive electrical circuit, or alternatively (b) a battery that charges a supercapacitor that drives the light source, (c) a battery that charges a capacitor that drives the light source, (d) a supercapacitor that drives the light source directly, or (e) a supercapacitor that charges a capacitor that drives the light source. The chemical battery may be non-rechargeable, such as alkaline, or re-chargeable, such as nickel-metal hydride (Ni-MH). A rechargeable battery would provide greater convenience and lower cost for the user. For topology regarding the alternative embodiment (c), a Ni-MH battery of about 50 $cm^3$ and 170 g would provide for about 15 minutes of operation. The capacitor would be about 50 $cm^3$ and 50 g.

Nickel-metal-hydride batteries are preferred over Li-ion batteries, which have substantially lower peak current capabilities. Ni—Cd batteries have undesirably low energy densities, although they do have lower series resistances. The Ni-MH batteries selected have a battery capacity of 3 Ampere-hours (Ah) at a voltage of 1.25 V and can easily generate the 500 pulses. These batteries are preferably and advantageously factory installed. That is, they are preferably only replaceable at the factory (e.g., during a refurbishment). An alternative consumer-replaceable battery embodiment, either disposable or rechargeable, involves a more complex design and higher cost. Such an alternative would involve battery contacts rather than soldered wires, and since the circuit of the preferred embodiment drives approximately 40 A, even 25 milliohms of contact resistance results in a one volt drop which is very undesirable in that it represents a considerable fraction of the total battery voltage available. Soldered battery contacts, which are preferred, have much lower resistance.

Electrical Circuit Details

Figure 11A:
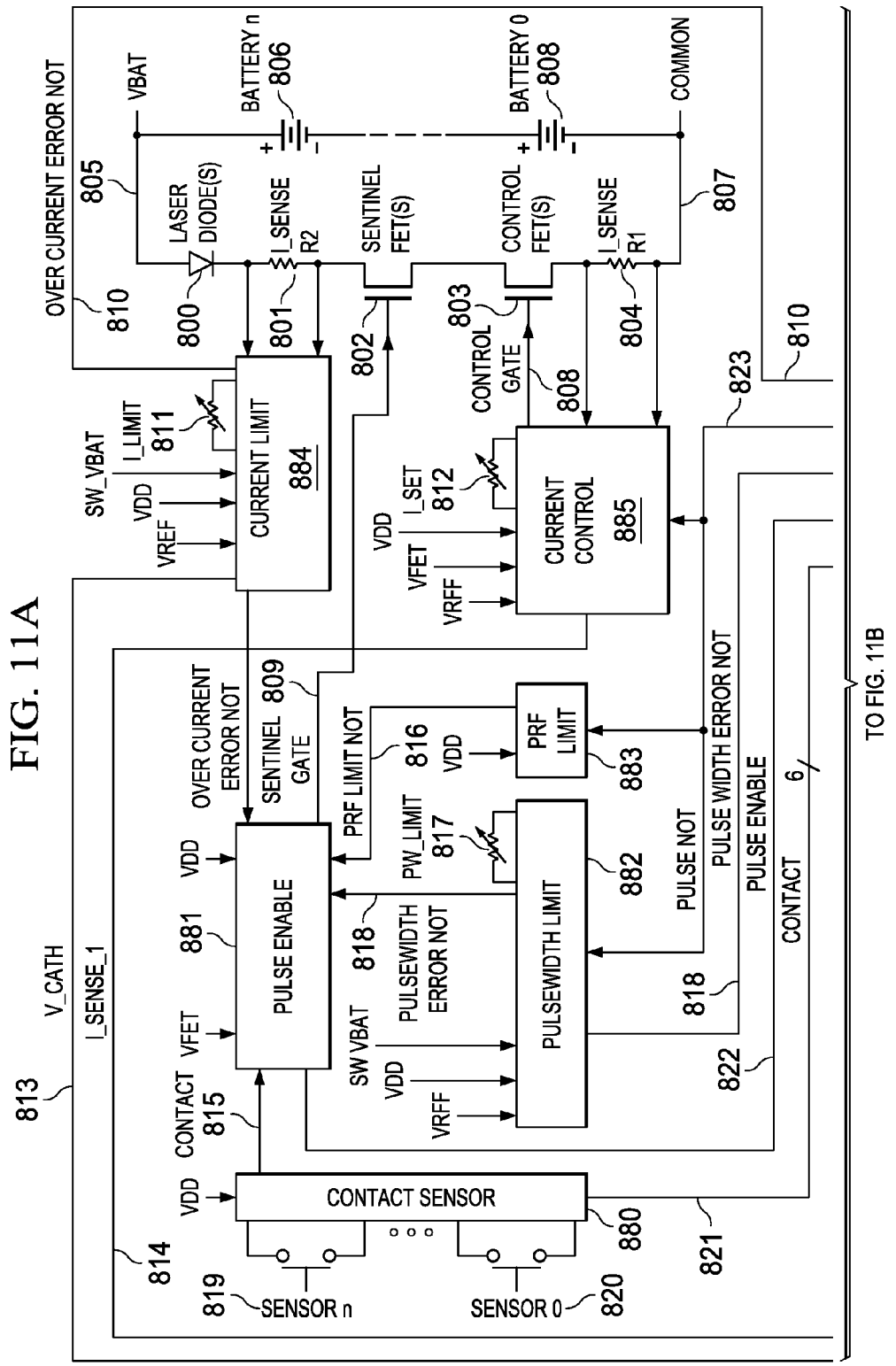
FIGS. 11A-11B schematically illustrates components of an electrical circuit in accordance with a preferred embodiment.
Figure 11B:
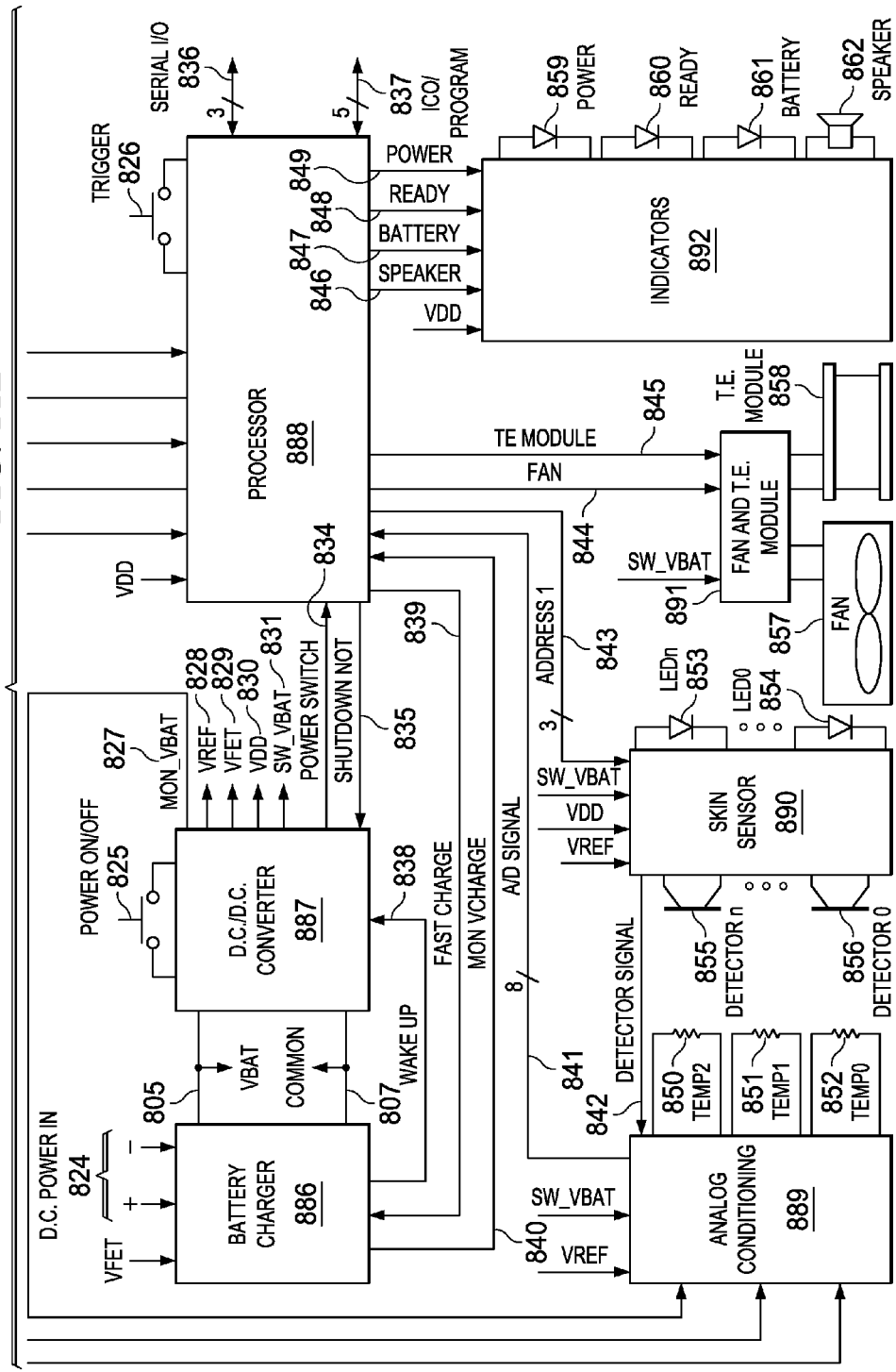

FIGS. 11A-11B shows the salient features of an electrical circuit in accordance with a preferred embodiment. Incidental components have been lumped into the various blocks of the circuit diagram. Although detail within each of the blocks is not shown, it is submitted that those skilled in the art can implement each of the blocks. The electrical circuit for powering and controlling the hair-regrowth-inhibition apparatus of the preferred embodiment is advantageously robust and efficient in driving a pair of laser diode bars within a cordless, hand-held, and self-contained device. The details of control electronics can vary greatly from the description below, and as schematically illustrated by the block diagram in FIGS. 11A-11B, and as shown in some more detail in FIG. 12 in accordance with a preferred and exemplary embodiment.

The controller of the device is the processor 888. Contained within the processor block is a microcontroller such as a P1C18LF452, manufactured by Microchip Technologies of Chandler, Ariz. Such a controller has many analog I/O, digital I/O, onboard read access memory (RAM), non-volatile memory (FLASH and EEPROM), and other features that make it inexpensive, small and convenient to use in a self-contained device that is relatively small and lightweight compared with conventional office-based devices. Although the device does not need to employ the use of a microcontroller, using one makes the capabilities of the device greater than it would be otherwise possible for a given size. Alternatively, it may be possible to use a custom application-specific integrated circuit (ASIC) for the processor and much of the other electronics. The trigger button 826 is used by the operator of the device to signal that a treatment pulse is desired. A trigger switch 826 may be omitted if the contact sensors 819 and 820 are used as a means to signal that the operator desires a treatment pulse. The processor 888 communicates with the other blocks through various signals. The processor may communicate with peripheral devices through a serial interface port 836. The processor may also have a programming port 837 by which the microcontroller may be programmed while preferably already soldered into the circuit. The programming port 837 may also be used with an in-circuit-debugger (ICD) to make design and debugging of the software more convenient.

A device in accordance with a preferred embodiment is powered by battery pack 806 and DC/DC converter 887. The number of batteries in the battery pack are sufficient to drive current through the laser diodes 800, or LED, flashlamp or other alternative light source, current sense resistors 801 and 804, and FET's 802 and 803. With great attention to parasitic resistances and creative circuit architecture, the preferred battery configuration includes five batteries rated at 1.2 V each and providing between 1.0 V and 1.5 V during the course of a discharge period. The voltage provided by the battery pack 806 is then between 5.0 V and 7.5 V.

The DC/DC converter 887 monitors the power button 825, a wake-up signal 838 from the battery charger 886, and a shutdown signal from the processor 888. The DC/DC converter 887 signals the processor 888 if the power button 825 is depressed via the power switch signal 834. A signal proportional to the battery voltage is communicated by the DC/DC converter 887 to the analog conditioning electronics 889 via the battery voltage monitor signal 827. The DC/DC converter 887 produces the various voltage levels required to power the other blocks of the circuit, namely a reference voltage 828, FET gate drive voltage 829, electronics supply voltage 830, and a switched battery voltage 831 that can be switched on and off by the DC/DC converter 887. The blocks in the diagram shown in FIGS. 11A-11B preferably each have a connection to the signal common 807 which may or may not be shown. Since any switch between the battery and other components would develop a parasitic voltage drop, the battery pack voltage provided to the laser diode loop is not switched independent of the sentinel FET(s) 802 and control FET's 803. The absence of a switch is shown via the battery signal 805.

The battery charger 886 is used to charge the battery pack 806. A commonly available low power, 9 VDC, 500 mA power adapter (not shown) can be connected at the DC power jack 824. The battery charger 886 has a fast-charge mode that charges the battery pack 806 with a current of about 450 mA and a trickle-charge mode that charges the battery pack 806 with a current of about 30 mA. The battery charge mode may be selected by the processor 888 via the fast charge signal 839. The processor is informed of the charge state of the battery pack via one of the signals in the analog signal bus 841. When a DC adapter is connected to the DC power jack 824, the battery charger can signal the DC/DC converter 887 to wake up via the wake-up signal 836 and can signal the processor 888 via the charge voltage monitor signal 840. Because the processor knows of the presence of the power adapter and the charge state of the batteries, an intelligent algorithm may be used for fast recharging of the batteries 806.

The analog conditioning circuitry 889 amplifies and converts the signal impedance, where necessary, of the various analog voltages that are sent to the processor 888. These signals include the laser diode cathode voltage 813, the current sense signal 814, the battery voltage 827, skin sensor detector signal 842, reference voltage 828, and voltages representative of the temperatures sensors 850, 851, and 852. The temperature sensors may be used to monitor the voltage of the finned heat exchanger; the cold side of the thermoelectric cooler elements 858; and the battery pack 806 and main circuit board. The conditioned analog signals are conveyed to the processor over the analog signal bus 841.

The purpose of the skin sensor circuitry 890 is to distinguish the presence of skin from other materials at the output aperture of the device. Light emitting diodes (LED's) 853 and 854 are used to illuminate the output aperture of the device. Remitted light is sensed by detectors 855 and 856. The processor 888 may select which LED to illuminate via address bus 843. The signal from detectors 855 and 856 are summed and communicated to the analog conditioning electronics 889 via the detector signal 842. The processor 888 can then compare the detector signal for each LED against the known expected value for skin. In this way, skin can be distinguished from many other materials. In a preferred embodiment, five LED's, emitting light in the blue, green, yellow, red, and infrared portions of the electromagnetic spectrum are used. Simple silicon phototransistors are used to detect the remitted light. Greater or fewer LED's may be used to increase or decrease, respectively, the degree to which the skin sensor can reliably distinguish between skin and other materials.

The fan and TE module electronics 891 provide power to the fan 857 and TE module 858. A fan signal 844 and TE module signal 845 from the processor 888 determine if the fan and TE module electronics 891 provide power to the fan 857 and TE module 858, respectively.

Visual indicators used to communicate with the operator include three LED's, power 859, ready 860, and battery 861. An audible indicator 862 is also preferably used to provide user feedback. The audible indicator is especially advantageous on a self-contained device since the operator may have difficulty seeing the device if used for self-treatment of areas of the body that do not enable the direct view of the visual indicators 859, 860, and 861. The power indicator 859 is used to signal to a person that the device is on. The ready indicator 860 signals that the device has initialized, is at the proper operating temperature, and that the user may begin treatment. The battery indicator 861 signals the charge state of the battery. All three indicators may be steadily illuminated (in addition to other preferred conditions) for the device to emit a treatment light pulse. The speaker 862 may be used to indicate power on, power off, a treatment pulse, and/or many other events through the use of different tones and various tone sequences and durations. Each of these indicators has an associated control signal from the processor 888: speaker signal 846, battery signal 847, ready signal 848, and power signal 849.

The contact sensor electronics 880 are used to detect contact of the output aperture and/or output window component of the device with a firm surface such as skin. One or more sensors, 819 and 820, may be used to sense contact of different portions of the output aperture. Three simple contact closures implemented through the use of a membrane switch commonly found in cell phone keypads, calculator keypads, or other electronics are used to detect contact in the device of the preferred embodiment. Other contact sensors using light, ultrasound, electrical resistively or other physical phenomena may be used. The state of the contact sensors are communicated to the processor 888 via the contact bus 821. The processor may use a complex algorithm for determining if sufficient contact is provided before it signals the other control electronics that a treatment pulse may be initiated and maintained. The contact sensor electronics 880 also may directly (and redundantly) signal the pulse enabling electronics 881 via a contact signal 815.

The current control electronics 885 provide closed-loop control of the current flowing through the laser diodes 800. The differential voltage across current sense resistor 1 (804) is monitored by the current control electronics 885 and is proportional to the current flowing through the laser diodes 800. This differential voltage is amplified and compared to a set point voltage that can be adjusted by the current setpoint resistor 812. The voltage on the gate of the control FET's 803 is continuously adjusted by the current control electronics 885 to ensure that the proper current is flowing. When no treatment pulse is desired, as indicated by the pulse not signal 823, the current control electronics 885 turns off the control FET's 803.

The current limit electronics 884 are used to monitor the current flowing through current sense resistor 2 (801). In a similar fashion as the current control electronics 885, the current limit electronics 884 amplifies the differential voltage developed across current sense resistor 2 (801) and compares this voltage with a voltage set by current limit resistor 811. If the current flowing through current sense resistor 2 (801) exceeds the limit, then an over-current error is signaled to both the pulse enable electronics 881 and the processor 888 via the over-current error not signal 810.

The pulsewidth limit electronics 882 are used to monitor the pulsewidth of the treatment pulse. An independent time base (different from that used by the processor 888) is used to ensure the duration of any treatment pulse does not exceed a time set by the pulsewidth limit resistor 817. If the processor 888 requests a pulse via the pulse not signal 823 that exceeds the pulsewidth limit then the pulsewidth limit circuitry 882 signals the processor 888 and pulse enable electronics 881 via the pulse width error not signal 818.

The pulse rate frequency (PRF, or repetition rate) limiting electronics 883 are used to ensure that treatment pulses are not emitted more frequently than desired, if sufficient time is not allowed by the processor 888 between pulses requested on the pulse not signal 823, then the PRF limiting electronics 883 indicates an error to the pulse enabling electronics 881 via the PRF limit not signal 816.

The pulse enabling electronics 881 ensure signals from other blocks indicate that the other blocks have satisfied their requirements prior to the initiation of a treatment pulse. These signals may include: contact 815, no over-current condition 810, no pulsewidth error condition 818, no pulse rate frequency (PRF) error 816, and the presence of a processor enable signal 822. If all of these enable signals are present, the pulse enable electronics 881 turns on the gate of the sentinel FET's 802 via a sentinel gate signal 809. If at any time any of the signals that are monitored by the pulse enabling electronics 881 indicate that the pulse should not continue, the sentinel FET's 802 are turned off by the pulse enabling electronics 881 and the output may be terminated mid-pulse.

The laser energizing circuit loop is shown comprised of the following elements: the laser diodes 800, battery pack 806, current sense resistor 1 (804), current sense control FET's 803, sentinel FET's 802, and current sense resistor 2 (801). This loop is shown in more detail in FIG. 12.

Figure 12:
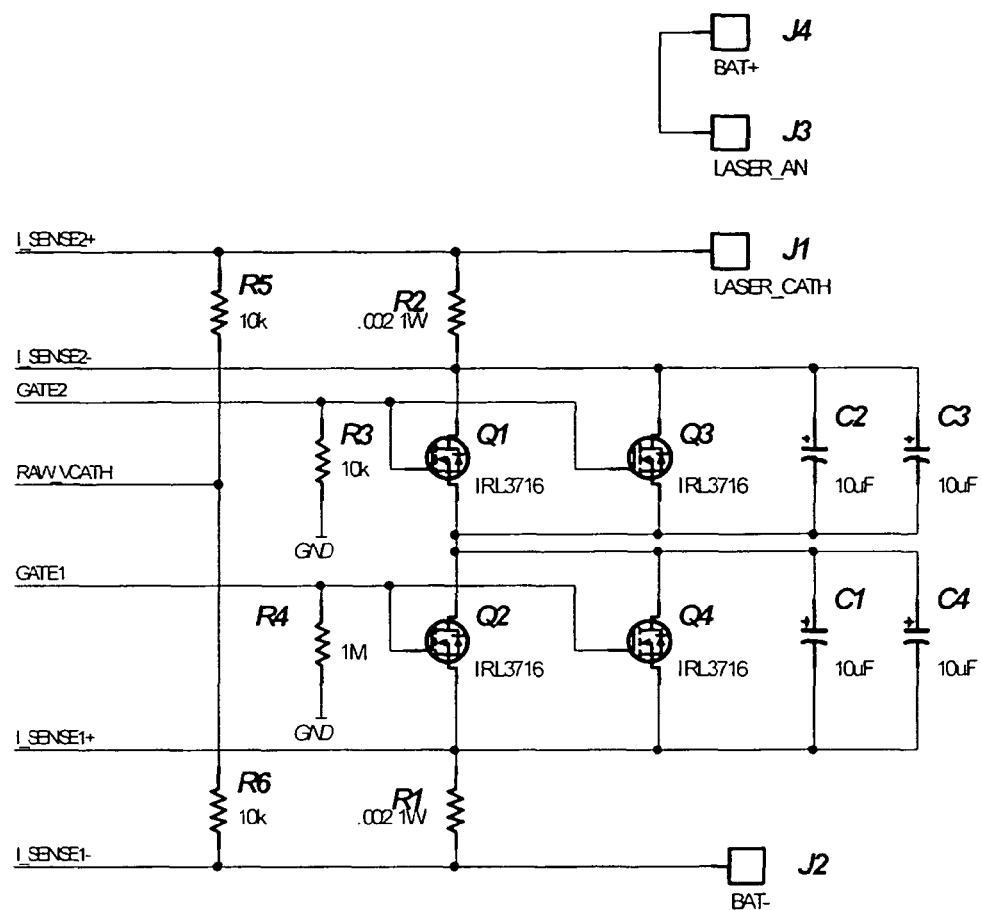
FIG. 12 schematically illustrate components of an electrical circuit for powering a laser diode light source with batteries through a FET-based switch in accordance with a preferred embodiment.

FIG. 12 shows the detailed schematics of the circuitry used to control the current to the laser diode bars. As indicated in FIG. 12, the battery pack 806 positive and negative electrodes are be connected at terminals J4 and J2, respectively. The laser diode bar cathode and anode are connected at terminals J1 and J3, respectively. Current sense resistor 1, R1, and current sense resistor 2, R2, are shown as 0.002 ohm resistors. The current control FET's are shown as a parallel connection of two FET's Q2 and Q4. The sentinel FET's are shown as a parallel connection of two FET's, Q1 and Q3. Resistors R3, R4, R5, and R6 are a part of the control electronics not shown discretely in the block diagram of FIGS. 11A-11B. Resistors R3 and R4 are connected to the gates of the sentinel FET's and current control FET's, respectively, so that the transistors turn off if either gate signal is for some reason disconnected. R5 and R6 are used to generate the laser diode cathode voltage signal 813 of FIGS. 11A-11B. The capacitors C1, C2, C3, and C4 are used to reduce the switching noise of the FET's and may not be necessary.

FIGS. 11A-11B and FIG. 12 show the salient features of an electrical circuit that can be used in accordance with a preferred embodiment. An advantageous feature of the design illustrated in FIGS. 11A-11B and FIG. 12 is that the laser diodes are powered directly by the battery pack. Here, the phrase, "powered directly," or, as used elsewhere herein, the phrase, "direct drive," are intended to mean that the instantaneous current flowing through the battery and the instantaneous current flowing through the laser diodes at a particular moment in time are substantially equivalent. The instantaneous currents differ only in that a small amount of current drawn from the batteries is used to power the control electronics. This architecture is markedly different from and advantageous over state-of-the-art laser systems and flash-lamp systems used for hair-regrowth inhibition due to various efficiencies that it provides.

Efficient Electrical Circuit Design

There is significant architectural advantage in the circuit of FIGS. 11A, 11B, and 12 over conventional pulse power circuits for delivering 40 ampere current pulses for energizing pulsed laser systems. Most circuits that are capable of delivering large current pulses rely on a main storage capacitor to store the electrical charge that is to be delivered during the pulse. For example, state-of-the-art hair removal systems like the LightSheer diode laser system, the Quantum flashed lamp system, and the Altus CoolGlide all have large banks of capacitors that are re-charged by a DC power source between pulses. In contrast, the system of the preferred embodiment includes a direct drive electrical circuit. As described above, the circuit directly switches current pulses from the batteries to the laser electrodes and does not include a main storage capacitor. Such main storage capacitor would involve a large bank of capacitors due to the low energy density of capacitors. Moreover, preferably no step-up or step-down transformer is used in the direct drive electrical circuit. This permits the size and weight of the apparatus of the preferred embodiment to be significantly less than a circuit including a main storage capacitor and/or transformer; and so in accordance with one of the goals of the design of the preferred embodiment, the additional size and weight of a main storage capacitor bank and transformer are avoided.

In addition, in capacitor-based systems, as current is delivered by a capacitor bank the stored charge decreases, and the voltage across the capacitors drops significantly (voltage charge/capacitance). The drop in voltage means that the initial DC voltage would need to be larger than desired so that there would be sufficient voltage available to continue to drive the system as the capacitors discharge. Thus, greater waste power would be generated across the control FET's 803 during the beginning of the pulse when the voltages have not dropped significantly. This would be inconsistent with the desire to have an energy-efficient circuit for the hand-held, cordless apparatus of the preferred embodiment. Further size and weight advantages are achieved in the direct drive electrical circuit of the preferred embodiment by avoiding use of a transformer.

Advantageous to the efficient use of power of this device is the use of laser diode bars 800. FIGS. 11A-11B, the symbol for a single diode is used to represent the series connection of one or more, and preferably two, laser diode bars. Laser diodes are much more efficient at converting electrical power to optical power than other lasers. In the preferred embodiment, two laser diode bars are connected in series. Laser diode 800 can be 40-watt, 808-nm packages manufactured by Cutting Edge Optronics, of St. Charles, Mo., par number ASM06C040W080810B80 or similarly packaged laser diode bars 800. A single diode bar 800 may be used if the optical power delivered is sufficient for therapeutic results. However, an efficient laser source is preferably combined with efficient batteries and circuit design in order to realize a self-contained and hand-held hair-regrowth-inhibition device.

Therefore, in the circuit of the preferred embodiment, the size of the batteries and the electrical circuit configuration are such that main storage capacitors are not required. Instead, the laser diodes are driven "directly" from the DC power source, or the battery pack. The usable voltage of the battery pack is reduced by the product of the current and the equivalent series resistance of the batteries (voltage=current×resistance), and so the batteries include advantageously small series resistances. Also, the batteries are capable of supplying approximately 40 A without damage. Although the most recent battery technology is lithium-ion, nickel-metal hydride or alternatively, nickel-cadmium, are preferred, because the maximum peak current draw is much greater than Li-ion can provide, for a given battery size. The choice of battery within battery pack 806 is strongly driven by its equivalent series resistance, or ESR. When drawing large currents from a battery, significant voltage can develop across this parasitic resistance. The voltage developed due to ESR is subtracted from the nominal battery voltage and so reduces the voltage available to circuits the battery is powering. The ESR is preferably low enough so that, when 40 A is drawn from battery pack 806, the resulting parasitic voltage drop is small compared to the voltage output of the battery pack 806. The "compact C" Ni-MH batteries have been selected for these and other reasons already mentioned. The batteries that comprise battery pack 806 may be Panasonic HHR300SCP Ni-MH rechargables, Panasonic P-170SCRP NiCd batteries, sold by Panasonic Matsushita Electric Corporation of America, Secaucus, N.J., or similar batteries.

Another advantage of the circuit design of the preferred embodiment is that voltage drops are minimized and/or avoided in many places. In FIG. 12, the laser diode bars are shown connected in series with the battery, FET's and current sense resistors. Minimizing the voltage developed across the components powered by the batteries is advantageous because this will determine the minimum voltage and hence the minimum number of battery cells that are included in the design and thus in part establish a lower limit on the weight and size of the apparatus. Voltage drops across the FET's, the current sense resistors, the laser diodes, the battery series resistance, and the circuit board traces and the other interconnections between these components have been taken into consideration.

The current sense resistors 804 and 801 are redundant current-sense resistors. The resistors are redundant for safety reasons. Each is used by a different sub-circuit to ensure that currents larger than desired are not permitted to flow through the laser diodes. Because of the large currents flowing through them (approximately 40 A each), an appreciable voltage will develop with even a small value of resistance. For this reason, components that are commonly thought of as resistors are not used, and instead, merely 1.5 inch lengths of 22 gauge copper wire are used. These lengths of wire have a resistance of only approximately 0.002 ohms, so that a voltage of approximately 80 mV develops across each of them when the laser is pulsed. Differential amplifiers within the current control electronics 885 and current limit electronics 884 serve to amplify the voltages to levels that are more readily used by the feedback circuitry.

The control FET's 803 are the FET's that control the current flowing in the circuit. Any excess voltage supplied by the batteries, that is, voltage greater than that involved in driving the desired current through the laser diodes, is dropped across the control FET's 803. However, as the batteries are discharged and the battery voltage decreases, there will not be excess voltage supplied by the battery, and so the voltage that develops across the FET's for the case when the batteries are nearly depleted is advantageously minimized in accordance with a preferred embodiment, because the FET's chosen have very low on-resistance ($r_{ds-on}$). The transistors shown, IRL3716 (International Rectifier Corp., El Segundo, Calif.), are actually 180 A/200 W transistors and are larger than are needed for merely current and power requirements. However, their low on-resistance is advantageous for this application. In addition, to lower the voltage developed across the FET's, two transistors in parallel are preferred instead of just one so that only approximately 20 A flows through each transistor.

The sentinel FET's 802 are used to shut off the current if an error condition exists (for example, if one of the control FET's 803 fail such that current flows when it should not). The sentinel FET's 802 are chosen with preferably the same criteria as the control FET's 803 with one exception. Since the sentinel FET's 802 are used only digitally to permit any current set by the control FET's 803 or restrict any current, the FET's are either tuned on "hard" or else turned off completely. In both of these states, little power is dissipated by the sentinel FET's 802 and so the transistor's packaging can have worse thermal performance than the packaging of the control FET's 803. For this reason, in FIG. 12, transistors such as IRF7832 (International Rectifier Corp.) may be used for transistors Q1 and Q3. IRL3716 transistors would be acceptable for use as FET's 802; however, they would undesirably add to the size, cost, and weight of the device.

The series resistance of the FET's is further reduced by enabling the circuit to supply relatively high voltages to the gates of each of the transistors. The on-resistance of FET's sharply depends inversely on the magnitude of gate-to-source voltage applied to the device. The DC/DC converter electronics 887 in FIGS. 11A-11B produce an FET gate drive voltage 829. In the preferred embodiment the gate drive voltage 829 produced by the DC/DC converter is 7.6 volts even when the battery pack voltage drops to less than 5 volts. This voltage is greater than the battery pack voltage and is present so that the FET gate-to-source voltage, Vgs, of each of the FET's can be driven to a greater value than would be possible if the magnitude of the voltage was limited by the battery pack voltage. This is especially true as the batteries become depleted and the battery voltage decreases to less than its fully charged level.

The control FET's 803 and sentinel FET's 802 are located in a way that minimizes the length of the traces and interconnects, isolates the current paths from sensitive circuitry, and provides a means of conductively rejecting the waste heat produced by the transistors to the finned heat exchanger 620 of FIG. 10. Wide, short traces and redundant traces on multi-layer boards achieve this. In a preferred embodiment, conventional electrical connectors are not used in the high current path so as to eliminate connector resistances. Instead, components are soldered at the factory. This represents a trade-off between ease of manufacture and repair with reductions in voltage drops throughout the circuit, wherein even milliohm parasitic resistances are avoided wherever possible.

Optical Parameters

Optical Output Specifications

Although particular output specifications for light pulses emitted from the apparatus of the preferred embodiment will be explained in more detail below, an exemplary device in accordance with a preferred embodiment may produce light pulses according to the following summary of parameters:

Output fluence: 18 J/cm$^2$
Spot size (or output aperture area): 1 cm$^2$
Pulsewidth: 0.300 s
Pulse repetition frequency: 0.5 Hz
Wavelength: 808 nm Therefore, the peak optical power is 60 W and coverage rate is 30 cm$^2$ per minute. These provide efficacious and practical treatment specifications. As will also be detailed below, these particular parameters fall within ranges for minimum and maximum quantities for the preferred device. These ranges preferably include:

Output fluence range: 4 J/cm$^2$ to 100 J/cm$^2$
Spot size (or output aperture area): 0.25 cm$^2$ to 2 cm$^2$
Pulsewidth: 0.010 s to 1 s, or more preferably 0.100 s to 0.500 s
Pulse repetition frequency: 0.1 Hz to 2 Hz
Wavelength: 700 nm to 1100 nm
Optical Peak Power (Peak Power): 10 W to 120 W.

Output Fluence

Throughout this patent application the term output fluence is intended to describe the fluence at the output aperture or output window of the dermatologic treatment apparatus. For purposes of clarification, the output fluence of the device is also termed below as $F_{source}$.

Among the most important output parameters, it is generally preferred to have a source fluence $F_{source}$ between 4 J/cm$^2$ and 100 J/cm$^2$. For pulse durations in the 0.3 ms to 3 ms range, temporary hair regrowth inhibition has been found clinically with output fluences as low as 4-5 J/cm$^2$. However, for pulse durations extending into the many tens to hundreds of milliseconds, it is believed that output fluences below about 10 J/cm$^2$ are unlikely to have significant effect. In the absence of actual clinical trials at these parameters, it cannot be established more precisely, and in any case will vary from person to person and even with body site on a single person.

Output fluences over approximately 100 J/cm$^2$ would be expensive to produce, unless an undesirably small spot size or excessively long pulse width is utilized. In addition, if this fluence is exceeded in less than 1000 ms, it is likely to be very painful or even cause burning of the skin. The fluence that the skin can tolerate is generally affected by at least four parameters. The first is the extent to which the epidermis is kept from rising in temperature while the target below is heated. In this regard, the preferred device includes a thermally-conductive contact surface made of sapphire, or alternatively incorporates some form of active cooling of the contact surface or the skin such as using a fan. Alternatively, cryogen spray may be used to cool the skin to be treated.

As discussed above, the safety of a home device is enhanced with lower output fluences. Further, higher output fluences, e.g., achieving twice the fluence with a same spot size involves twice the number of laser diode bars and probably twice the batteries. Thus the practical design constraints of a self contained, hand-held, cordless, self-care device on safety, weight, size, and cost suggest that output fluences less than about 100 J/cm$^2$ are desired.

The laser diode bars of the light source 140 preferably emit light pulses such that a majority of the energy is in the spectral band of 700 nm to 1100 nm, and particularly around 800 nm, although visible wavelengths may also be used; bandwidths between approximately 1 nm and 10 nm; pulse durations preferably between 3-10 milliseconds (ms) and one second, and more preferably between 100 ms and 500 ms and particularly around 300 ms, at a repetition rate of between 0.1 Hz and 2 Hz, and particularly between 0.25 Hz and 1 Hz.

Wavelength

Another significant parameter is the wavelength of the light. In general, the longer the wavelength, at least over a range between 400 nm and 1100 nm, the higher the fluence tolerated by the skin, because the absorption of light by the melanin present in skin decreases monotonically with increasing wavelength over this range.

In a hair-regrowth-inhibition procedure, melanin in the hair shaft and follicle absorbs light, resulting in thermal injury to the follicle and delayed regrowth. Thus one might assume that light having a shorter wavelength would be preferred, since these wavelengths are more strongly absorbed. However, the melanin in the skin overlying the hair follicle also absorbs more light at these wavelengths, reducing the fluence tolerated by the skin. Theoretical calculations and clinical results have determined that optimum results for hair-regrowth inhibition are obtained for most skin types when the light source has an output in the spectral band between 700 mm and 1100 am. Wavelengths longer than 1100 nm, in addition to having very low melanin absorption, also become problematic due to water absorption, which begins to limit optical penetration depth making the apparatus less efficient.

The preferred wavelength of emission of the light source 140, preferably made up of one or more laser diode bars, is thus between approximately 700 nm and 1100 nm. In the case where a flashlamp is utilized as the light source, particularly for other dermatologic procedures, a wavelength of 500 nm to 1100 nm may be preferred, since flashlamps are inherently broadband sources, and thus a broader wavelength range may be involved for achieving the desired fluence.

In addition, if blood vessels are targeted, the increased absorption of blood at wavelengths in the region of 510-580 nm make somewhat shorter wavelengths desirable.

In the case where LED's are utilized as the light source, higher power LED's may be available at wavelengths below 700 nm; thus a wavelength range of 600 nm to 1100 nm may be preferred.

Bandwidth

The pulses emitted by the light source 140 are generated preferably by energizing the laser diode bars with 40 A for less than half a second. Therefore during the application of this energy, the laser diode material warms from about 20° C. to about 50° C., or a difference of 30° C. over the duration of the pulse. The emission wavelength particularly of III-V emitter materials such as $Al_xGa_{1-x}As$ varies with temperature. For example, $\lambda(T)$ may vary by about 0.3 nm/° C. Therefore, the emission wavelength may vary by about 9 nm during the pulse, and the effective bandwidth of the pulse is then generally about 1 nm and may be between about 5 nm and 10 mm. Where used herein, bandwidth is defined as the full-width half-maximum of the energy spectrum.

Sources such as diode lasers or LED's, that typically have bandwidths of less than 40 nm, are generally preferred over flashlamps because they have higher electrical-to-optical conversion efficiency.

Pulse Repetition Frequency

The repetition rate of pulses, or pulse repetition frequency, is preferably between approximately 0.1 Hz and 2 Hz, and particularly between around 0.25 Hz and 1 Hz, or between one pulse every second to one pulse every four seconds. A repetition rate any faster than 1-2 Hz is not desired owing to the expense and weight of a device capable of producing pulses this rapidly. Moreover, the self-care user of the device, whether it is a person at home applying the light to his or her own skin, or a user treating another person's skin, would find it difficult to manipulate the apparatus over the application area of the skin at higher repetition rates. On the other hand, a repetition rate slower than one pulse every four to ten seconds would render the coverage rate of the apparatus annoyingly slow for home use. That is, the application time simply becomes too long even for small treatment areas.

A higher repetition would translate into a higher coverage rate or more skin area treated per minute, which is desirable. However, a higher repetition rate also involves a higher average input power since the average optical power is higher. This higher electrical power requirement, in addition to increased volume, weight and cost, creates a problem of waste heat from the laser diode bars of the preferred apparatus.

Pulse Duration

Another important parameter is pulse duration. If the epidermis is kept from rising excessively in temperature, the energy can be continued to be applied into the hair follicle over a time that is roughly the thermal relaxation time of the stem cell region of the follicle, e.g., for approximately 100 ms to 500 ms. With contact cooling, the epidermis is kept from getting too hot; and much more fluence, or energy over a given area, can be applied into the dermis if it is applied over a longer time period.

The preferred pulse duration of the apparatus is above 3-0 ms and below approximately one second or even 500 ms. Pulse durations below around 10 ms, and particularly below 3-8 ms, are not desired for the light-based hair-regrowth-inhibiting apparatus, because to achieve adequate energy deposition in such a short time requires high optical peak powers. For example, application of an energy density of 20 $J/cm^2$ in a 0.8 $cm^2$ spot area (16 J) in a 10 ms pulse involves a optical peak power of 1600 W. This very high peak power is expensive to generate. For example, with diode laser bars each having a optical peak power of 30 W, over 50 bars would be used, and this is too many for a self-contained, hand-held and cordless device. It is also more difficult to render the device eye-safe, which is important in a home use, self-care device, because the maximum permissible exposure (MPE) is much less for short pulses such as these. That is, the MPE scales as the pulse duration to the three-quarter power, or $t^{0.75}$, and for eye safety, it is therefore generally more desirable to have longer pulses at desired output fluences than short ones. The thermal relaxation time of the hair follicle is generally at least 10 ms and may be as high as 100 ms to 600 ms for the stem cells surrounding the hair follicle, and so for the reasons provided, it is particularly desired to have pulse durations at least as long as this thermal relaxation time, such that a particularly preferred minimum pulse duration may be 100 ms or more.

On the other hand, as pulse durations get too long, such as above between 600 ms and one second, heat which is initially deposited into the melanin-laden hair shaft diffuses beyond the hair follicle. Somewhere in this pulse duration regime a transition gradually occurs from spatially-selective heating of just the follicle (and surrounding stem cells) to so-called bulk-heating of the dermis. If the pulse duration is increased at constant energy (or constant fluence), the optical peak power eventually gets so low that the target does not get sufficiently hot to cause hair-regrowth inhibition. If the peak power is kept constant as the pulse duration is increased, the fluence can get so high that the bulk heating becomes painful and/or may even cause skin burns.

It is noted that use of the term pulse, or pulse duration, is intended to include not only a single pulse in the conventional sense, but also a train of discrete pulses ("sub-pulses") or modulated pulse over the same time duration. In general, for the purposes of this patent application, these sub-pulses are considered to be one pulse if the time duration between the start of the first sub-pulse and the end of the last sub-pulse in a group is less than the time period between groups of such sub-pulses.

Optical Peak Power

It would be difficult to effect even temporary hair-regrowth inhibition, e.g., temporary delay in hair regrowth, if the optical peak power of the light source is below approximately 10 W. At peak powers below this threshold, very long pulse durations would be involved to approach a lower limit on output fluence, e.g., 4 J/cm$^2$. For example, to get an output fluence of 10 J/cm$^2$ in a 0.8 cm$^2$ spot (i.e., and output energy of 8 J) a pulse duration of 800 ms is required at a peak power of 10 W.

As peak powers of over approximately 100-20 W, considerable energy can be generated in a pulse having a more desirable duration and a useful spot size. However, higher peak powers are difficult to obtain in an inexpensive, self-contained, battery-powered self-care device.

Spot Size

There are multiple undesirable effects if the spot size, or area of skin illuminated by light pulses propagated from the apparatus, is too small. (In cases where the output aperture of the device is close to, or in contact with, the skin, the spot size on the skin and the output aperture of the device are approximately equal in size.) First, a very small spot, e.g., less than 0.25 cm$^2$, renders only one hair to be treated at a time in a hair-regrowth-inhibition procedure. In addition, some sort of visual targeting would be involved to ensure that the spot is indeed over a target follicle. Second, a small spot implies a very low coverage rate; i.e. to cover a given number of square centimeters of skin containing unwanted hairs, the smaller the spot size the longer the treatment time. This problem can be mitigated to some extent by increasing the pulse repetition rate, but doing this involves more electrical power, more expense, and more weight. Third, while a small spot size would appear to be quite advantageous in the sense that a low energy can still generate a high fluence on the skin surface (since fluence is energy divided by area), the fluence at some depth within the skin where the target cells are located is substantially reduced by scattering within the skin. The smaller the spot size, especially below about 0.25 to 0.5 cm$^2$, the more pronounced the effective lessening of fluence at depth relative to fluence at the surface. In short, if one goes to too small a spot, the end result can be either burning of the epidermis (to get enough fluence in the dermis) or no efficacy due to inadequate fluence at depth.

At the other end of the range, a larger spot size is desirable primarily because of enhanced coverage rate. For example, at a spot size between 2 cm$^2$ and 4 cm$^2$ spot size per pulse, entire legs could be treated in less than 30 minutes, assuming a pulse repetition frequency of roughly one pulse per second. However, for a given output fluence and pulse duration, the optical peak power required scales linearly with the spot size, and the cost and weight become prohibitive once the spot size gets above approximately 1.0 to 2.0 cm$^2$.

Skin Color

A parameter that is not a characteristic of the output pulses of a dermatologic treatment device, but that has a significant influence on the effect of light-based treatment, is skin color. People with fair skin, e.g., of Scandinavian descent (so-called Type I), can handle perhaps six to eight times the fluence on the skin compared to a black person with so-called type VI skin. With good contact cooling, a several hundred millisecond pulse, an 800 nm source and Type I skin, an output fluence as high as 100 J/cm$^2$ would be usable without significant epidermal injury. However, most Caucasians have type II or type III skin, and 50 J/cm$^2$ might be the damage limit. For darker skin, the limit may be closer to 30 J/cm$^2$. Although in a preferred embodiment, only a fixed output fluence is generated by the device (as well as only a single pulse duration being factory set), due to the various skin types of users, an alternative embodiment of the apparatus includes means of lowering the output fluence either continuously or discretely in a high-medium-low embodiment, where the high setting still corresponds to a maximum potential fluence at the eye of a person below the maximum permissible exposure (MPE) as detailed below. The advantage would be that darker-skinned persons may find the high setting painful, and therefore might prefer the medium or low setting, while still maintaining acceptable efficacy.

Eye Safety

Eye Safety Overview

Increased divergence and reduced spatial coherence, and resulting increase in eye safety, is accomplished by incorporating into the path of the beam of light within the apparatus, a diffusing material through which the light travels prior to leaving the apparatus, as in the second embodiment shown in FIG. 2A. Alternatively, the divergence may be increased and spatial coherence reduced by incorporating into the device a diffusing surface upon which the beam strikes prior to leaving the device, as in the third embodiment shown in FIG. 2B.

To compensate for any light that is absorbed within the apparatus by the introduction of the diffuser, the output power from the light source within the apparatus can be increased. Alternatively, the diffusing material or diffusing surface can be chosen to be substantially non-absorbing and the light source housing can be constructed so that the internal surfaces are substantially non-absorbing so that substantially all of the light will be emitted from the output aperture of the apparatus, albeit after one or more scattering events from the diffusing material or diffusing surface, or light source housing.

Although the fluence of the light emitted by the output aperture will generally decrease as it propagates away from the apparatus due to the divergent nature of the beam, many of the chromophores within the skin that are targeted by light-based treatments are near the surface of the skin. If the target is much closer to the surface of the skin than the size of the output aperture of the apparatus, there will be little decrease of fluence at the chromophore due to divergence of the emission. Since skin itself is a highly scattering medium for much of the electromagnetic spectrum, the decrease in fluence at the target when using a very divergent source with little or no spatial coherence is relatively insignificant when compared to the fluence at the target produced by a collimated light source that has equal fluence at the surface of the skin; provided that the distance from the output window or aperture of the source to the target beneath the skin surface is small compared to the lateral dimension of the source (e.g., the diameter of the output window).

Calculations of Maximum Permissible Exposures and Fluences at the Eye of a Person To evaluate eye safety under the ANSI, IEC or ICNIRP guidelines, two values are calculated and compared. The first is the Maximum Permissible Exposure (MPE). This value is the fluence or irradiance that is considered safe for the human eye, measured at the cornea. The actual value of the MPE varies greatly depending on the characteristics of the light source in question; specifically, the source wavelength, pulse duration, coherence, and, if incoherent (e.g., from a diffuse source) the angle formed by the dimension of the source and its distance from the cornea (the so-called angular subtense that determines the size of the corresponding image of the source on the retina; see International Standard IEC 60825.1, "Safety of Laser products—Part 1: Equipment classification, requirements and user's guide", Edition 1.2, August 2001; p. 11.).

The second value "$F_{cornea}$" is the fluence produced at the cornea from a particular light source, as measured through a pair of apertures limiting the angle of acceptance to 100 milliradians (see IEC 60825.1, above, p. 40, NOTE 2, sub-note d.). The value of $F_{cornea}$ depends upon both the fluence produced by the device at its output (the "output fluence"), as well as how the light diverges from the output as it propagates toward the eye. For any light source, if $F_{cornea}$ is less than the MPE for all possible distances between the source and the eye, the device is considered eye-safe. Conversely, a light source that produces, at any particular distance, a value for $F_{cornea}$ that exceeds the MPE is considered hazardous.

For wavelengths of light between 400 nm and 1,050 nm, and pulse durations between 18 microseconds and 10 seconds, the Maximum Permissible Exposure (MPE) at the cornea is given by the following equation:

$$\text{MPE}(J/cm^2) = 1.8 \times 10^{-3} t^{0.75} C_4 C_6 \quad [\text{Eq. 1}]$$

where t is the pulse duration in seconds;

$C_4$ is a correction factor for the wavelength λ of light, having the following values:

for λ greater than 400 nm but less than 700 nm (visible light), $C_4=1$;

for λ greater than 700 nm but less than approximately 1100 nm (near-infrared light), $$C_4 = 10^{0.002(\lambda - 700)} \quad [\text{Eq. 2}]$$

note that C4 increases from a value of 1 at 700 mm and has a value of 5 at 1,050 nm;

$C_6$ is a correction factor that is equal to 1 for coherent sources (this is strictly correct for sources that have a spatial coherence near the diffraction limit; for multimode sources or for arrays of coherent sources the calculation is more complex); and for diffuse, extended sources is given by $C_6 = \alpha/\alpha_{min}$ where $\alpha_{min}$ is equal to 1.5 milliradians and α is the angular subtense of the source, i.e.

$$\alpha = 2\tan^{-1}(d/2r) = d/r \quad [\text{Eq. 3}]$$

where d is the diameter of the source and r is the distance from the source to the cornea. Equation 3 applies only up to an angular subtense of 100 milliradians; above this angle, a value of 66.7 is used for $C_6$.

Two cases are considered below to exemplify the eye hazard associated with typical current devices for dermatologic treatment:

1. A visible, coherent source (e.g., a laser), having a circular output aperture of one centimeter squared (diameter of 1.13 cm) and a 30 millisecond pulse duration;

2. An incoherent, directed source (e.g., a flashlamp) having a rectangular output aperture of 1 cm by 2 cm and a 30 ms pulse duration.

Example 1

Visible, Coherent Source (e.g., Laser)

Figure 4:
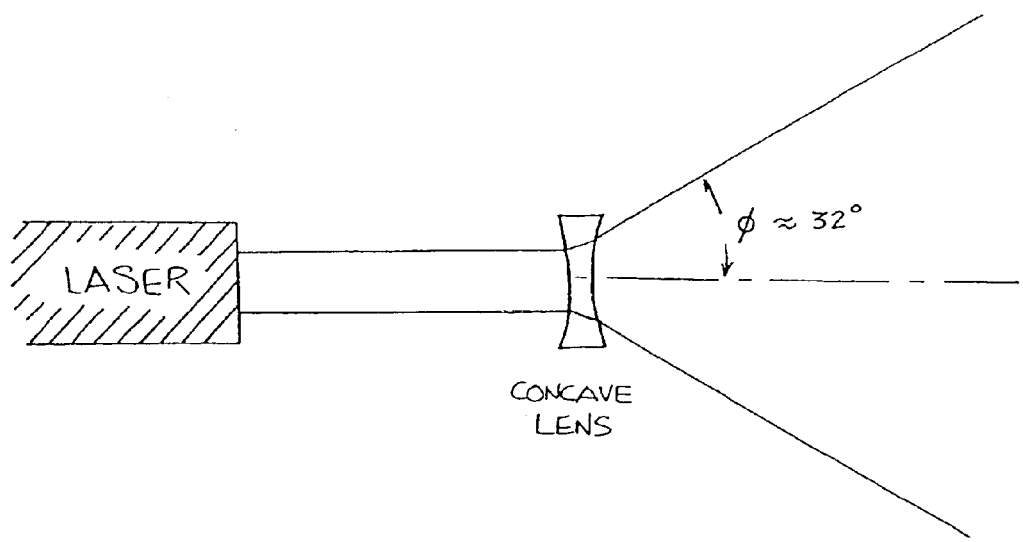
FIG. 4 schematically illustrates the divergence of a laser beam transmitted through a bi-concave lens.

For a source of diameter d=1.13 cm, the angular subtense of the source varies depending on the distance r from the eye; however, because in this example the source is a laser in the visible region of the spectrum (in this example it is assumed that the laser is highly spatially coherent), both $C_4$ and $C_6$ are equal to 1, and the maximum permissible exposure at the cornea given by Equation 1 is:

$$\text{MPE} = 1.8 \times 10^{-3} t^{0.75} C_4 C_6 = 1.8 \times 10^{-3}(0.072)(1)(1) = 1.3 \times 10^{-4} \text{ J/cm}^2$$

or 130 microjoules per square centimeter. This fluence is of the order of 100,000 times lower than the fluence involved in the therapeutic dermatologic treatment of typical skin problems such as hair-regrowth inhibition. It is of course true that the fluence exiting the 1 cm² laser aperture could be much higher than the 130 μJ/cm² figure calculated above; for eye safety it is understood that only the fluence at the cornea, $F_{cornea}$, be no higher than this figure for the laser source in this example. But such a source, if it is to be efficacious for the dermatologic treatments mentioned, would produce at least a few joules per square centimeter at its exit aperture, and it is illustrated below that this type of source will always exceed the MPE at some distance. For example, suppose for eye safety reasons that the beam is designed to be highly divergent upon leaving the exit aperture; for example, by passing the beam through a very fast f/0.8 concave lens as shown in FIG. 4. (An f/0.8 lens has a focal length equal to 0.8 times its diameter.) This beam exits the lens at an angle φ of about 0.56 radians, or 32 degrees. The fluence at a distance r from the exit aperture is given by (this is approximately correct for a Gaussian beam from a diffraction-limited laser):

$$\text{Fluence } F = 4Q/\pi(r\varphi)^2 \quad [\text{Eq. 4}]$$

Where Q is the energy of the source. So for a source of 5 J/cm² output fluence from a 1 cm² aperture, the fluence at a distance of, for example, 20 cm (i.e. the output aperture of the device is 20 cm from the eye) is approximately 50 mJ/cm², still several thousand times above the MPE. Any adjustment factors for pulse duration or longer wavelength to increase the MPE would not be nearly sufficient to make this device eye safe; for example, increasing the wavelength to 1050 nm and the pulse duration to 300 ms results in only a roughly 30-fold increase in MPE, to about 4000 μJ/cm² (i.e., increase due to pulse duration is $(300/30)^{0.75}$ or about 5.6; increase in λ from visible to 1050 nm increases C4 from 1 to 5; so combined increase is 5.6 times 5, or about a factor of 28).

Example 2

An Incoherent, Directed Source (e.g., a Flashlamp)

A popular device for hair-regrowth inhibition as well as for facial "rejuvenation" utilizes a flashlamp with visible and near infrared output and an exit aperture of 1 cm by 2 cm, and an output energy of 80 J (40 J/cm²) (see Hode, L, "Are lasers more dangerous than IPL instruments?" Lasers in Surgery and Medicine, Supplement 15, 2003, p. 6; and poster presentation at corresponding conference). Such sources typically have a directed output of about plus or minus 20 degrees, i.e. a solid angle Ω of about 0.4 steradians. If it is assumed that (very roughly) half of the output energy is in the visible, and half is in the 700 nm-900 nm range, a value of the wavelength correction factor $C_4$ of ~1.3 is appropriate. The conclusions of this section are insensitive to this parameter in any case. Because this device emits incoherent light, the correction factor $C_6$ appropriate for "extended sources" can be greater than one, and in fact will reach 66.7 when the angular subtense of the source is 100 milliradians, i.e. when the source is roughly 15 cm from the eye (see International Standard IEC 60825-1, p. 52. For non-circular sources the angular subtense is the arithmetic mean of the of the larger and smaller angular dimensions of the source). It should be noted that, once the source subtends an angle greater than 100 milliradians (i.e. comes yet closer to the eye) the hazard to the eye remains the same, because although the irradiance on the cornea increases, the image area on the retina increases proportionally. From Equation 1:

$$MPE(J/cm^2)=1.8\times10^{-3}C_4C_6=1.8\times10^{-3}(0.030)^{0.75}\times 1.3\times66.7=11\ mJ/cm^2$$

The fluence F at a distance r from a source of energy Q directed into a solid angle $\Omega$ is approximately:

$$F=Q/(r^2\Omega)=80/(15^2\times0.4)=890\ mJ/cm^2$$

Thus, in this case $$F_{cornea}=890\ mJ/cm^2$$

or approximately 80 times in excess of the MPE; still an extreme eye hazard. To make this device eye safe the fluence would have to be reduced by this factor, i.e., from 40 J/cm² to ~0.5 J/cm², significantly below the fluence necessary to perform therapeutic photothermal dermatologic treatment.

A Proposed Device in Accordance with a Preferred Embodiment

Figure 5:
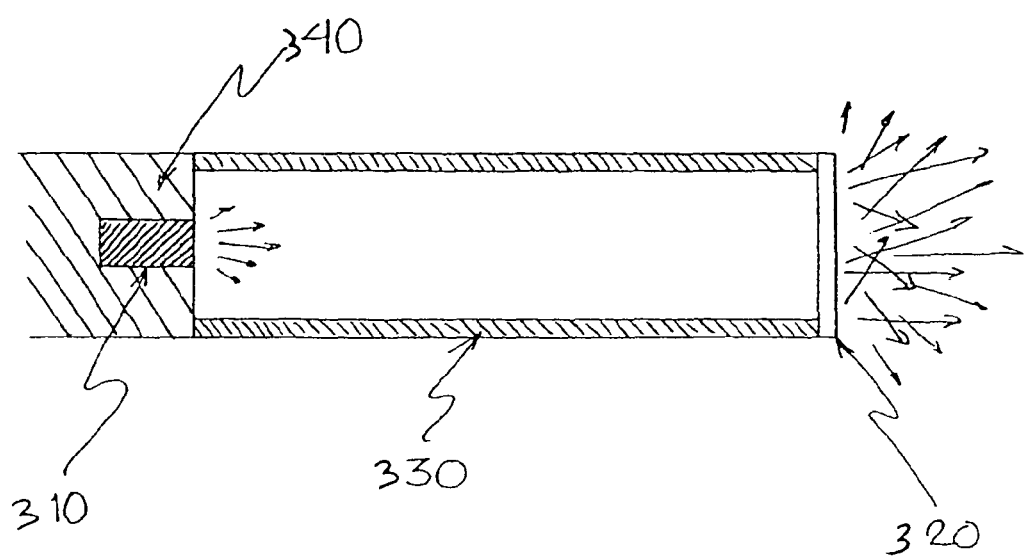
FIG. 5 schematically illustrates a hair-regrowth-inhibiting apparatus in accordance with the second embodiment.

Calculations analogous to those above can be done for an embodiment of the invention herein, as follows. As shown in FIG. 5, a light source 310, which can be either a coherent source such as a laser or an incoherent source such as a flashlamp, impinges on a diffuser 320. The diffuser in turn emits the scattered light preferably as an approximately Lambertian source in the forward direction (see Earle Brown, Modern Optics, Reinhold Publishing Corporation, 1965; p. 225). Light backscattered from the diffuser toward the laser or flashlamp can be reflected to impinge once again on the diffuser by incorporating reflective walls in the chamber 330 and on the surface of light source holder 340 that faces chamber 330. It should be noted, however, that such reflective walls only serve to improve the overall efficiency and spatial uniformity of the device and are in no way essential to the invention. In addition, the diffuser 320 need not be located at the exit aperture, but may be recessed within chamber 330; in this case the walls of chamber 330 between the diffuser 320 and the exit aperture should be non-absorbing. It should also be noted that the diffuser has the added advantage of removing any "hot spots" from the light source; i.e., a source such as an array of diode laser emitters has much higher integrated radiance in some directions than in others; such localized variations will be smoothed out by a diffuser. In this embodiment a disk diffuser of the Oriel type is described, but the invention can also be effected with a different type of diffuser, as defined earlier.

For the sole purpose of providing a concrete example, let us assume that the device has a circular output aperture of area one square centimeter, as in Example 1 above. Let us further assume that the device has a wavelength of 800 nm. From Equation 2, $C_4$ is equal to 1.58. As in Example 2 above, we also assume that the device is at a distance from the cornea such that the source (e.g., the diffuser located at the output aperture) subtends an angle of 100 milliradians ($C_6$=66.7). For a source of 1.13 cm diameter (1 cm² area) this distance is about 11.3 cm. Under these conditions, from Equation 1:

$$MPE(J/cm^2)=1.8\times10^{-3}t^{0.75}C_4C_6=1.8\times10^{-3}(0.072)$$
$$(1.58)(66.7)=13.7\ mJ/cm^2$$

For a Lambertian source, the fluence at a distance r (when looking directly into the source) for a source of energy Q is given by $$F(J/cm^2)=Q/\pi r^2 \qquad [Eq.\ 5]$$

(see International Standard IEC 608251, p. 79);

Thus, for our source at a distance of 11.3 cm, the fluence at the cornea is equal to the MPE of 13.6 mJ/cm² when Q is equal to 5.5 joules. Since our source has an aperture of 1 cm², this corresponds to a source fluence of 5.5 J/cm². Thus our invention can have a source fluence of 5.5 J/cm² for providing an intended photothermal injury to the skin and yet have an output below that which would result in an exposure to the eye in excess of the MPE:

$$F_{source}=5.5\ J/cm^2$$

$$F_{source}=MPE=13.7\ mJ/cm^2$$

As stated above, for this source to be considered eye safe, the fluence at the cornea from the device must be less than the calculated MPE for all distances between the source and the eye, not merely the distance chosen in the above example. This can be shown to be true, as follows.

For distances less than 11.3 cm (i.e. as the output aperture of the source is drawn closer to the eye, causing the angular subtense of the source to exceed 100 mrad) the MPE remains the same. With decreasing distance, the fluence from the source increases, but $F_{cornea}$, remains constant because, as described above, it is measured through apertures limiting the angle of acceptance to 100 mrad. Thus, if $F_{cornea}$ is less than the MPE at a source distance corresponding to an angular subtense of the source of 100 mrad, it is also safe at lesser distances.

Considering now the opposite case, where the source is moved farther from the eye than 11.3 cm, two cases will be considered: that case where the distance from the source to the eye is such that its angular subtense is more than 1.5 mrad but less than 100 mrad (for a source of 1.13 cm diameter, distances between 11 cm and 750 cm) and that case where the source subtends an angle of less than 1.5 mrad (distances of greater than 750 cm). In the first case, the MPE decreases linearly with increasing distance, but from Equation 5, $F_{cornea}$ decreases as the square of the distance. Thus, if $$F_{cornea}<MPE\ at\ \alpha=100\ mrad$$

then $$F_{cornea}<MPE\ for\ 1.5\ mrad<\alpha<100\ mrad$$

Considering now the last case, where the distance from the source to the eye is such that the angular subtense is less than 1.5 mrad (for the source above, distances of greater than 750 cm), the values for MPE and $F_{cornea}$ vary as follows: as the distance increases, the MPE remains constant, but as above, $F_{cornea}$ continues to decrease as the square of the distance. Thus one can conclude that the above source is safe at any distance.

As introduced above, one or both of the following additional features is preferably included to allow even higher device fluences that are nonetheless still eye-safe. These features include an increase of the pulse duration of the light (e.g., from 30 ms to 300 ms), and an increase in the wavelength of the light (e.g., from visible to infrared); both of which result in a higher MPE for the eye and thus allow an increased therapeutic output that is still eye-safe. The benefits of each of these elements (diffuse source, extended pulse duration, and longer wavelength) can be quantified, as described above and below. In short summary, however, pulse durations in excess of 100 ms and wavelengths above 700 nm are preferred, while as maxima, pulse durations are maintained at or below 500 ms and wavelengths below approximately 1100 nm.

In order to further enhance the utility of the device and its use, the pulse duration can also be extended to preferably 300 ms from 30 ms, or in a preferred range between 100 ms and 500 ms. In a number of therapeutic dermatologic procedures including light-based hair-regrowth inhibition, pulse durations of 300 ms or greater are and/or may be an effective optimum. From Equation 1, in this case the MPE increases by a factor of $(0.3/0.03)^{0.75}$ or about 5.6. Thus the light source in our example can have an output fluence 5.6 times greater than calculated above, or approximately 31 J/cm$^2$, and it will still not exceed the MPE at any distance.

Note that this calculated value of 31 J/cm$^2$ for a source fluence that is eye-safe agrees well with the corresponding value derived from the Accessible Emission Limit (AEL) as determined by the CDRH for a Class I laser device. Devices below the Class I AEL are considered to be eye-safe and therefore require no specific warning labels or other controls. From Table I of 21 CFR 1040.10, a laser device meets the Class I AEL if its integrated radiance is less than the value below:

$$AEL = 10 k_1 k_2 t^{1/3} \text{ J/(cm}^2 \text{ sr)}.$$

Since, for our source,
$k_1 = 1.56$;
$k_2 = 1$; and
$t^{1/3} = (0.300)^{1/3} = 0.67$,
then, AEL=10.4 J/(cm$^2$ sr).

For a Lambertian source, the source fluence (radiant exposure) is related to the integrated radiance L through the formula:

$$F_{source} = \pi L;$$

thus $$F_{source}(\max) = (3.14 \text{ sr})(10.4 \text{ J/(cm}^2 \text{ sr})) = 32.6 \text{ J/cm}^2.$$

Thus, the device will be below the Class I Accessible Emission Limit if the source fluence is less than 32.6 J/cm$^2$, a value that agrees well with the 31 J/cm$^2$ calculated earlier from the IEC limits for Maximum Permissible Exposure. There may be further calculations or methods for determining an eye safe limit as may be required by the FDA or a different standards setting organization or in a different country or setting. Although any of these eye safe limits are understood to be at least approximately the values calculated as the AEL and the MPE limits, the value used may differ and devices constructed accordingly may differ in their output limitations. Any such adhered to or acknowledged reasonable eye safety limitation is intended to be included within the meaning and use of the term "eye safe" as used in the present application.

Further Optical Design Considerations

The addition of a diffuser to a light-based dermatologic device to permit therapeutic fluences at the skin surface while ensuring eye-safe operation is by no means limited to the preferred and alternative embodiments described above and elsewhere herein. For example, a device for the treatment of acne using blue or other visible light can be made eye safe at therapeutic fluences by the addition of a diffuser; and a device for repigmentation of skin, or treatment of psoriasis or vitiligo, using ultraviolet light (290 nm to 400 nm) can also be made much safer with a diffuser added to the output aperture. In general, such devices contain incoherent sources with a directed output; i.e. the output beam expands from the output aperture by ~±20 degrees, corresponding to a solid angle of about 0.4 steradians. By the addition of a diffuser, the output propagates into a full 2π steradians; if the diffuser creates a Lambertian distribution of the light (as is the case with an Oriel-type diffuser) the angular dependence of the output fluence will have the well-known cosine dependence, while other elements also described as diffusers for the purposes of this application may have a more general variation of fluence with viewing angle. When typical devices without a diffuser (i.e. devices which may have, for example, a light output spreading into ~0.4 steradians) are viewed on-axis, i.e. directly into the source, the addition of the diffuser (backed by a chamber having reflective walls) reduces the fluence at the cornea by the ratio of (0.4/π), or about 0.13, without affecting the fluence of the device when applied to the skin. Thus a device that produces a fluence at the cornea which exceeds the MPE by up to eight times can be made eye safe by the addition of a diffuser.

It should be noted that the fluence can be increased by up to an additional factor of two (while still remaining eye-safe) by altering the output distribution of the light from Lambertian to that approaching a uniform source. This can be effected, for example, by creating concentric micro-grooves (either by diamond-machining of sapphire or casting of plastic) such that an increased fraction of the light is refracted into higher angles, as illustrated at FIG. 3B, or incorporating a point source and mirrored chamber design as illustrated at FIG. 3D.

The output pulses of the apparatus described above are described in terms of energy (i.e., radiant exposure and integrated radiance) rather than in terms of power (i.e., irradiance and radiance); but the invention applies equally to devices and/or methods characterized either by energy or power.

Alternative Embodiments

Preferred and alternative embodiments of the invention may also include any one or a combination of the following elements. First, as described earlier, the heat removal element may be a thermal battery that is "recharged" (i.e., heat is removed) or replaced prior to use and absorbs heat during use. The thermal battery may be a phase-change material, such as ice, certain paraffin-like waxes or salts such as TEA29 from TEAP Energy, or may be a high-heat capacity material like copper or aluminum or water, or may be a compressed gas or liquid that cools by expansion to lower pressure. Second, a pigmentation sensor may be included that senses the amount of pigment in the skin. Such a sensor may be used to adjust output parameters such as pulse duration or pulse energy or to prohibit operation for pigmentation levels higher than a pre-selected threshold. Third, a means of operation that is sliding, rather than sequential spot-wise treatment, may be employed. By sliding, it is meant that the device is operated by continuously sliding the active area of the device across the skin. The light may be delivered in pulses or continuously. The device may provide feedback to the user to help maintain dosimetry within a given range and/or may have a mechanism or internal feedback, such as provided by an optical or mechanical sensor, to help maintain dosimetry within a given range. Fourth, non-contact cooling may be employed, such as spray cooling or liquid cooling or cooling with an gel applied to the skin. Fifth, reflective or diffusive surfaces or elements on or within the device may be used that may redirect light that has been scattered back to the device from the skin back into the skin. Such redirection of remitted light may occur by specular or diffuse reflection, such as from a partially transmissive diffuser near the output aperture or from reflective surfaces within or on the device. (As stated earlier, the term "reflective" is used in this context to include remissive surfaces.)

In addition to hair-regrowth inhibition, the invention can also be advantageously applied to other dermatology applications, including treatments for acne, benign pigmented lesions, vascularity, skin texture, skin wrinkles, and "photo-rejuvenation" which is generally accepted in the field to mean skin treatment for pigmented lesions (including brown and red spots), vascularity (including the destruction of small blood vessels), and/or skin tone, skin texture, and skin wrinkles. For these applications, the invention may be modified from the preferred embodiment hair-regrowth-inhibition device to make the device more optimal for the application. Some modifications to preferred and alternative embodiments described herein may be understood by those skilled in the art for alternative application in the above fields. For example, for the treatment of acne, a wavelength between 350-450 nm may be chosen for its photodynamic effect on the porphrins produced by the acne bacteria. Alternatively, a wavelength in the range 1000-1800 nm may be chosen to match the absorption spectrum of sebum, a major component in acne. Likewise, for "photorejuvenation" a broad-band source, such as a flashlamp, may be used in order to simultaneously treat vascular and pigmented lesions and improve skin tone, texture, and wrinkles. For photorejuvenation, somewhat shorter wavelengths have been shown to be efficacious; e.g., 500-1100 nm. For dermatologic applications, the output fluences are generally desired to be greater than 4 J/cm$^2$ to be efficacious and the light is generally not eye-safe at these levels, although in accordance with a preferred embodiment, a diffuser is employed to reduce the maximum fluence at a person's eye to below the MPE.

Also, "divergent" light sources such as diode laser light sources are referred to herein. Light is defined herein as "divergent" when the divergence angle $\alpha$ is greater than approximately ±6 degrees, where the divergence is defined as the geometric mean of the half-angle formed between the principal propagation axis (z-axis) and the full-width half-maximum (FWHM) energy axes in the x and y coordinate directions. That is, if the divergence from the z-axis in the x-direction is $\pm\alpha_x$ and the divergence in the y-direction is $\pm\alpha_y$, then the divergence $\pm\alpha$ equals the square root of the quantity $\alpha_x$ times $\alpha_y$. For example, diode laser bars typically have a FWHM beam divergence of about ±20 degrees in one axis and about ±5 degrees in the other axis, so have a typical divergence of about ±10 degrees as defined here. Thus, diode laser bars are a divergent light source. Diode lasers in general, flashlamps, and LED's are also typically divergent sources. A divergence value of 6 degrees clearly differentiates "divergent" sources, such as diode lasers and flashlamps, from "collimated" sources, which in practice have some divergence but typically less than 1 degree. Divergent light sources are superior to other light sources for achieving eye safety, in that a significant portion of the light from such divergent sources striking the diffuser is already partially directed at significant angles from the principal propagation direction. Thus the task of the diffuser to spread the light into large angles is simplified.

While an exemplary drawing and specific embodiments of the present invention have been described and illustrated, it is to be understood that the scope of the present invention is not to be limited to the particular embodiments discussed. Thus, the embodiments shall be regarded as illustrative rather than restrictive, and it should be understood that variations may be made in those embodiments by workers skilled in the arts without departing from the scope of the present invention, as set forth in the appended claims and structural and functional equivalents thereof.

In addition, in methods that may be performed according to preferred embodiments herein and that may have been described above, the operations have been described in selected typographical sequences. However, the sequences have been selected and so ordered for typographical convenience and are not intended to imply any particular order for performing the operations, unless expressly set forth in the claims or as understood by those skilled in the art as being necessary.

We claim:

1. A dermatologic hair-regrowth-inhibiting apparatus, comprising:
    a housing;
    one or more diode laser bars;
    an electrical circuit disposed within the housing, the electrical circuit comprising:
        one or more batteries that energize the one or more diode laser bars to produce a light pulse;
        a direct drive circuit such that during the light pulse the current flow through the one or more batteries is substantially equal to the sum of the current flow through the one or more diode laser bars; and
        a closed-loop current control system comprising:
            one or more control field effect transistors (FET's) electrically coupled to the one or more batteries and the one or more diode laser bars, each FET having a gate;
            a voltage supply coupled to the gate of each control FET's; and
            a controller configured to control the voltage supply to control a voltage applied at the gate of each control FET to thereby control a current flowing through the one or more diode laser bars.

2. The apparatus of claim 1, wherein the voltage supply applies a greater voltage at the gates of the control FET's than a battery voltage supplied by the one or more batteries.

3. The apparatus of claim 1, wherein the controller of the closed-loop current control system is configured to continuously control the current flowing through the one or more diode laser bars by:
    monitoring a differential voltage across a current sense resistor, which voltage is proportional to the current flowing through the one or more laser diode bars;
    amplifying the monitored differential voltage;
    comparing the amplified differential voltage to a set point voltage; and
    controlling the voltage applied to the gates of the control FET's based on the comparison.

4. The apparatus of claim 3, wherein:
    the closed-loop current control system comprises a current setpoint resistor; and the controller of the closed-loop current control system is configured to control the current setpoint resistor to dynamically adjust the set point voltage.

\* \* \* \* \*